(12) United States Patent
Heslot et al.

(10) Patent No.: US 6,342,353 B1
(45) Date of Patent: Jan. 29, 2002

(54) METHOD FOR CHARACTERIZING NUCLEIC ACID DUPLEX

(75) Inventors: François Heslot; Baptiste Essevaz-Roulet; Ulrich Bockelmann, all of Paris (FR)

(73) Assignee: Centre National de la Recherche Scientifique (CNRS) (FR)

( * ) Notice: Subject to any disclaimer, the term of this patent is extended or adjusted under 35 U.S.C. 154(b) by 0 days.

(21) Appl. No.: 09/367,890

(22) PCT Filed: Feb. 20, 1998

(86) PCT No.: PCT/FR98/00340

§ 371 Date: Nov. 4, 1999

§ 102(e) Date: Nov. 4, 1999

(87) PCT Pub. No.: WO98/37234

PCT Pub. Date: Aug. 27, 1998

(30) Foreign Application Priority Data

Feb. 21, 1997 (FR) .............................................. 97 02092

(51) Int. Cl.⁷ .......................... C12Q 1/68; C12P 19/34; C12M 1/34; G01N 33/00; C07H 21/02
(52) U.S. Cl. ....................... 435/6; 435/91.1; 435/287.2; 436/94; 536/23.1
(58) Field of Search ........................ 435/6, 91.1, 283.1, 435/287.1, 287.2, 288.1, 183; 436/94; 536/23.1, 24.3, 24.33, 25.3

(56) References Cited

FOREIGN PATENT DOCUMENTS

EP 0 397 416 11/1990
WO WO 94/23065 10/1994

OTHER PUBLICATIONS

Jean–Louis Viovy et al., "Séquençage de l'ADN par ouverture mécanique de la double hélice: une évaluation théorique", C.R. Acad. Sci. Paris, Sciences de la vie/Life Sciences, vol. 317, No. 9, pp. 795–800, (1994).
A. Bensimon et al., "Alignment and Sensitive Detection of DNA by a Moving Interface", vol. 265, pp. 2096–2098, (1994).
C. Desmaze et al., "In Situ Hybridization of Fluorescent Probes on Chromosomes, Nuclei or Stretched DNA: Applications in Physical Mapping and Characterization of Genomic Rearrangements",Cellular and Molecular Biology, vol. 41, No. 7, pp. 925–931, (1995).
S.B. Smith, "Direct Mechanical Measurements of the Elasticity of Single DNA Molecules by Using Magnetic Beads", Science, vol. 258, pp. 1122–1126, (1992).
B. Essevaz–Roulet et al., "Mechanical Separation of the Complementary Strands of DNA", Proc. Natl. Acad. Sci., vol. 94, pp. 11935–11940, (1997).
A. Noy et al., "Stretching and Breaking Duplex DNA by Chemical Force Microscopy", Chemistry & Biology, Research Paper, vol. 4, No. 7, pp. 519–527, (1997).

*Primary Examiner*—Ethan Whisenaut
*Assistant Examiner*—Frank Lu
(74) *Attorney, Agent, or Firm*—Finnegan, Henderson, Farabow, Garrett & Dunner, L.L.P.

(57) ABSTRACT

The invention concerns a method for characterizing nucleic acid duplexes comprising two sequences of nucleic acid at least partially paired, characterized in that it consists in recording at least a signature of said duplexes, which is linked to the force variation required for separating, receptively re-pairing, said two sequences, and in comparing the resulting signature with references.

49 Claims, 15 Drawing Sheets

METHOD FOR CHARACTERIZING NUCLEIC ACID DUPLEX

The present application is a U.S. national stage application of PCT/FR98/00340, filed Feb. 20, 1988, which claims priority to French Application No. 97 02092, filed Feb. 21, 1997.

The present invention relates to a method allowing the identification of signatures corresponding to a specific sequence of double-stranded nucleic acid.

In the field of DNA sequence analysis, the present invention relates to a method which makes it possible to accelerate or bypass the process of genomic DNA sequencing, a problem which is of considerable industrial interest. The method according to the present invention allows the identification of specific signatures of a sequence on a long DNA fragment. This method makes it possible in particular to rapidly search for the presence of particular structures in the base sequence and/or the quality of the pairings which may be partial and, in particular, have mismatches. This method also allows analysis and comparison of the genomic differences among various patients.

It is understood that the invention also applies to single-stranded DNA-single-stranded DNA duplexes, perfectly paired or not perfectly paired, or alternatively to single-stranded DNA-single-stranded RNA duplexes, perfectly paired or not perfectly paired, or alternatively to single-stranded RNA-single-stranded RNA duplexes, perfectly paired or not perfectly paired. Furthermore, the duplex may consist of the at least partial re-pairing of two single strands obtained from samples of different origins. Finally, the invention also applies to the secondary structures of a sole single-stranded DNA or of a sole single-stranded RNA.

To clarify the disclosure, there is used in the text which follows the specific example of a double-stranded DNA, it being understood that the above generalizations can be easily achieved by simply developing the methods described.

A "signature" makes it possible to "characterize" a DNA sequence.

By way of example, the pairing of the G and C bases involves three hydrogen bonds, whereas the pairing of the T and A bases involves only two bonds; under these conditions, if the DNA double helix is mechanically opened by separately pulling the ends of two strands on the same side of an isolated DNA molecule, it can be expected that the signal corresponding to the forces exerted depends on the sequence.

Thus, the implementation of the present invention has made it possible to demonstrate that the separation of two paired strands essentially results in the obtaining of a "signature", that is to say a set of specific and local information which is linked to the sequence and/or to the state of pairing.

Unexpectedly, during the opening of a duplex, the signal in force may exhibit in particular serrated structures, with a gentle rise and a more abrupt descent, where the opening occurs, in part, in short bursts. The forces measured during the opening therefore exhibit a set of particular characteristics, or signature, a complex combination of the sequence where the regions rich in GC are harder to open than the regions rich in AT, and of the mechanical stiffness of the system (molecular construction and system of measurement), which come into play to induce events where several contiguous bases open more rapidly.

By modifying the mechanical stiffness of the system, it is possible to increase (at low stiffness), or decrease (at high stiffness) the effects of instability and to obtain a set of signatures for the same sequence.

Thus, a "signature" does not constitute a base-to-base sequencing of an entire sequence, but makes it possible to obtain a set of specific and local information, linked to the sequence and/or to the state of pairing.

Measurements of force on isolated molecules of DNA currently constitute a very active field (see references 1 to 11). For a range of forces extending from one subpicoNewton to tens of picoNewtons, which forces are typically involved in weak molecular interactions, sensitive devices for the measurement of forces such as optical tweezers (Svoboda et al., 1993; Yin et al., 1996) or flexible microneedles are being increasingly used.

In a typical configuration intended to open DNA, the molecules may be specifically anchored on two solid substrates (microscope slide, micropipette, microparticle). One of the ends being attached and the other being connected, for example via a particle, to a device for measuring force.

Patent WO 94/23065 describes a device for measuring force, base-to-base, during mechanical opening of DNA using an atomic force microscope.

However, the base-to-base resolution is fraught with basic limitations linked to thermal noise (Thompson al., 1995; Viovy et al., 1994).

Moreover, carrying out the opening in practice exhibits operational difficulties, in particular:

the design of the molecular construction, the chemistry of the surfaces and their preparation, the manner of selecting the place where the measurement is carried out.

In particular, it is crucial, in order to carry out these experiments, to reduce:

the level of adsorption of the study molecule on the surfaces (microscope slide or particle);

the adhesive interactions between the particles and between the particles and the surfaces.

Finally, since a single measurement can take several tens of minutes, it is necessary to have a very efficient selection mechanism in order to macroscopically identify the most useful points so as to carry out the measurements despite the fact that the chemistry of the surfaces is imperfect, and of course, despite the fact that the constructions themselves may be imperfect.

The present invention includes the aspects relating to the chemistry of the surfaces and the specific constructions so as to obtain satisfactory results.

More particularly, the present invention relates to a method for characterizing a nucleic acid duplex comprising two at least partially paired nucleic acid sequences, characterized in that at least one "signature" of said duplexes, which is linked to the variation in force necessary to unpair, respectively re-pair, said two sequences is recorded, and in that the signature obtained or some characteristics thereof is compared with references.

It is understood, by way of example, that a reference may consist of another measurement, a combination of several measurements, or alternatively of a numerical calculation, for example such as that which will be described in the text which follows, or alternatively a combination of the preceding cases.

"Nucleic acid duplex" is understood to designate any type of DNA/RNA duplex as mentioned above.

More particularly, the present invention relates to a method characterized in that the 5' end of one of the strands of the duplex is attached to a support 1 and the 3' end of the other strand of the duplex is attached to a support 2, the variation in force necessary to unpair, respectively pair, said sequences being measured by moving apart, respectively bringing closer, said supports 1 and 2, characterized in that, during the attachment, the point of attachment of the 3' end on the support 2 and the point of attachment of the 5' end on the support 1 are linked together by a molecular string having a length of at least 0.03 μm, and preferably of between 0.5 and 30 μm.

Within the framework of the present invention, and to clarify the notations, the 5' end of one of the strands of the duplex will be called "5' end of the duplex" and the 3' end of the other strand of the duplex will be called "3' end of the duplex", and, in this definition, the strands can of course be reversed.

"Molecular string" is understood to designate both the distance calculated on the molecule (it being possible for the latter to be folded), for example the spacer arm (mode I), and the spatial distance (measured in particular along the strands between the two points of attachment (mode II).

Supports 1 and 2 may also be interchanged in the developments which follow.

Advantageously, the method in accordance with the invention is characterized in that the structure of the duplex is locally modified in particular by the creation of a triplet, a complex or the attachment of a protein.

A few terms which will later be used in accordance with their respective definition are defined below.

Given that the experiments are carried out in a buffer, a "well" is a component intended to contain a small volume of buffer and it may advantageously incorporate or contain one or more components, which are detachable or otherwise, called "slides".

The "slide" is a solid component which is flexible or rigid in nature and has the following characteristic features:

a) At least part of this slide is in contact with an essentially aqueous buffer, and at least a fraction of this part in contact is functionalizable on a surface of at least 0.01 μm², and preferably between 1 μm² and 10 cm².

b) The slide being in place in the well, it is possible to bring closer, in order to obtain an image of the functionalizable part in contact with the buffer, either an immersion microscope lens in aqueous media, or an immersion microscope lens in oil and, in this case, the slide may be advantageously thin, flat and substantially transparent.

By way of specific example, the slide may be a microscope coverslip, a polymer coverslip or a particle maintained by a micropipette.

A well may be advantageously designed so as to be able to receive a "micropipette".

A "micropipette" is a solid component, flexible or rigid in nature, of which one end may be attached to a fixed or moving system, and of which at least the other end is intended to be immersed in a liquid. It is substantially elongated in appearance and its characteristic diameter is greater than 0.01 μm, preferably between 0.1 μm and 2 mm, and it may be advantageously hollow.

The supports envisaged may be either slides, particles, micropipettes or a component of an apparatus for measuring force.

In the method according to the present invention, the manipulations are preferably carried out with specific molecular constructs, advantageously attached, between a slide for example, and microparticles, or alternatively by attachment of the ends to two particles.

This method essentially comprises two embodiments.

More particularly, in the first embodiment (mode I) of the method, it is a method in which the 3' end of the duplex to be characterized (respectively the 5' end) is attached to one of the supports via a spacer arm having a length of at least 0.03 μm, preferably of between 0.5 and 30 μm.

In this method, one of the characteristics is that the DNA duplexes intended to be opened are not directly attached to a support, but are attached via at least one spacer arm placed either on the support 1, or on the support 2, or on both. Indeed, the use of a spacer arm makes it possible to select the site and/or the time for carrying out the measurement. It is possible, for example, to adapt to this type of molecular construct the selection and measurement technique used by Smith et al. (1996). It is also possible to carry out multiple anchorages on a slide.

Under these conditions, the particles linked to the slide via a molecular construct have some freedom of movement. Of course the length of the spacer arm may be advantageously adjusted in relation to the spatial resolution of the system for locating the position of the beads.

When a weak force is simply applied to the particles, the DNA will not open and it will be possible to observe the following characteristic movement:

A particle moves but is then blocked in its movement by the presence of the spacer arm. The characteristics of this movement make it possible to select the systems of interest on which a measurement cycle can be applied and make it possible in particular (i) to eliminate the imperfect attachments; in particular if the particle starts to adsorb to the slide, or if the DNA starts to adsorb, the characteristics of the movements will be more limited, and therefore different; (ii) during the slightly abrupt phase of sticking of a measuring microneedle, the relative freedom of movement of the particle makes it possible to avoid the pulling out of the point of attachment.

The spacer arm may consist of double-stranded DNA, of 100 to 500 bases, that is to say about 0.03 μm to 0.2 μm, but preferably the spacer arm will correspond to 1 kb or will even comprise from 5 to 100 kb, which will approximately correspond to a clearance of 1.5 to 30 μm, but it is also possible to envisage spacer arms which would not consist of a double-stranded DNA, but which would consist of other components of the synthetic polymer type, of the protein type or alternatively of other, for example polysaccharide, polymers.

Thus, just before the measurement, the sample which is under the microscope consists of:

nonattached mobile particles;

particles which are immobile on the slide;

particles with a limited movement.

Of course, only the latter particles are of interest. In order to improve the selection of these particles, it is possible to apply to them either a magnetic field gradient, in particular a magnet, if particles have been chosen on which a magnetic gradient exerts a force, or a fluid-type field, or an electric field, or an electric field gradient. And the particles which have a zone of movement which corresponds to the expected extension of the spacer arm in the absence of undesirable attachments of the spacer arm or of the DNA sequence with the surface or with the particles themselves, are chosen at this time.

In general, the length of the spacer arm, which makes it possible to locate the particles which may be the subject of a study, is known. Techniques intended to allow grafting on the ends of molecular constructs are known; they are essentially systems using a ligand/receptor combination, or alternatively covalent bonds. Preferably, the ends to be grafted are biotinylated or functionalized with a ligand such as dig, whereas the glass slides for example, or the particles are respectively coated with avidin or streptavidin or an antidig antibody.

In general, to attach the end of the nucleic acid sequence to the support, it is possible to use:
- a covalent interaction
- an antigen/antibody interaction
- a ligand/receptor interaction
- an avidin or streptavidin/biotin interaction.

The optional attachment of the particle or of the support to the device for measuring force may be carried out by any means, in particular by bonding, as above, but also by sticking or by magnetic influence using appropriate beads.

More specific constructs will be described in the examples below.

The spacer arm may of course be placed either on the first support, a slide consisting of a glass surface for example, but it is possible to envisage an attachment to the particle via a spacer arm; in this case, the method is characterized in that the 5' end of the duplex to be characterized, respectively the 3' end, is attached to the support 2 via a spacer arm having a length of at least 0.03 $\mu$m, but preferably of between 0.5 $\mu$m and 30 $\mu$m; in this case, one of the ends of the duplex may be directly attached to the slide. In order to further improve the method, it is possible to envisage the use of two spacer arms, one in relation to the surface or support 1, the other in relation to the particle or support 2.

In the second embodiment (mode II), the support 2 is attached to the 3', respectively 5', end, while the duplex to be characterized has been at least partially denatured and the ends of the two unpaired nucleic acid sequences comprising it have been partially spatially moved apart by a distance of at least 0.03 $\mu$m, preferably of between 0.5 and 30 $\mu$m.

Preferably, the free ends of the duplex are linked by a hairpin-shaped sequence which makes it possible to denature the entire duplex.

More specifically,
- the duplex being blocked by a hairpin, each of the free ends is functionalized, for example, with biotin and dig,
- then a particle comprising, for example, streptavidin is attached to the corresponding end,
- this bead is then immobilized by any, for example mechanical (micropipette), means,
- the complex is then denatured and the whole is placed in a stream of fluid,
- the end not attached to the bead moves away and an anti-dig treated bead is for example attached to this end; this bead can be approached by any means, in particular optical tweezers.

In the preferred embodiment mode I, the spacer arm will consist of a double-stranded DNA, for example a double-stranded DNA obtained from the $\lambda$ phage.

The DNA duplex (DNA 1) for which it is desired to obtain a signature according to the present invention should be connected to the spacer arm. Preferably, the duplex is digested with at least one restriction enzyme, which makes it possible to know the nature of its ends, blunt or cohesive, and in this case the cohesive sequence.

It is then easy for persons skilled in the art to attach the segment to the spacer arm (lambda DNA and the like), for example by a cassette-type system.

An exemplary embodiment is given in FIG. 2B which is a spacer arm cassette system, DNA 2 is a double-stranded DNA of $\lambda$ phage completed by:

(i) dig functionalization on one side: this is carried out, for example, with the aid of oligo 3, which is a Cos sequence dig functionalized in 3' and is covalently attached by hybridization and then ligation;

(ii) the system of adaptors oligo 1 and oligo 2: oligo 1 has a Cos sequence and is attached by hybridization and ligation to DNA 2; oligo 2 is 3' functionalized with biotin; it has a sequence which is complementary to part of oligo 1 and can therefore attach to it by simple hybridization, the free end of the oligo 1-oligo 2 duplex is chosen so that it is cohesive with the cleavage of the DNA-1 DNA with a restriction enzyme.

By hybridization and then ligation, a covalent bonding of the two 3' and 5' strands of one end of DNA 1 is obtained: the 3' strand to oligo 2 and the 5' strand to oligo 1.

In the final construct, the dig end is attached to a support 1 and biotin to a support 2. The support 1 may be, for example, a glass coverslip coated with antidig, and the support 2 may, for example, be a microbead coated with streptavidin.

The opening of DNA 1 may be obtained by moving the support relative to the bead, which draws its 3' strand linked to the bead, and its 5' strand linked to the coverslip by the spacer arm DNA 2. In this example, it is naturally possible to interchange the positions of the dig and biotin functionalizations.

A cassette assembly as has just been described by way of example may be a component of a diagnostic kit, so as to obtain the construct which allows opening by a simple hybridization-ligation operation.

By way of example, such a technique, applied to the opening of the lambda phage DNA (DNA 1, FIG. 2), with a spacer arm consisting of the double-stranded DNA of a lambda phage (DNA 2, FIG. 2), is described.

In the final construct, the oligo 2 connector may have a free nonpaired region, close to biotin, so as to facilitate subsequent reaction with the microparticles. The entire construct is linked by ligation steps after the various hybridization steps, leaving the possibility of opening the molecule at the biotinilated end. Naturally, other combinations of ligands and of receptors may be chosen, or alternatively multiple ligands of the same type may be used in place of a single one (Cluzel et al., 1996; Strick et al., 1996). Finally, the spacer arm may be naturally placed either between support 1 and DNA to be opened (example given here) or between DNA to be opened and support 2, or a combination of preceding cases. An additional feature of the method is introduced as regards the other end of the molecule to be opened. It may be capped with a cohesive hairpin-shaped oligonucleotide (hairpin-oligo) which avoids the two strands separating when the end of the opening process is reached. This makes it possible to repeat complete opening-closing cycles. It is also possible not to use this additional component and to carry out a partial opening while avoiding completely unpairing the duplex, which advantageously makes it possible to repeat partial opening-closing cycles.

Signature Modification

As will be seen in the text which follows, the signature depends on the total stiffness of the system, that is to say of the measuring system and also of the molecular construct, in particular that of the single strands of the opened molecule. This stiffness parameter can be advantageously varied in order to obtain different signatures for the same sequence.

1) Stiffness of the Measuring System

As regards the lever, it is easy to change it for levers of different stiffness. In the case of a measurement by an optical tweezer, this may be obtained, for example, by simple modification of the intensity or of the position of the trapping laser. Naturally, other modes of operation, in particular with retroaction (for example Finer et al, 1994; Svoboda et al., 1993; Yin et al., 1996), may be advantageously used.

Two examples are given:
(i) In one of these cases, the position of the tweezers may be automatically adjusted by retroaction to prevent the movements of the bead. The variation in the force during the opening results in a variation in the position of the trap.
(ii) In the other example, the intensity of the tweezers may be controlled by retroaction so as to keep the position of the bead fixed. The variation in the force during the opening results in a variation in the intensity of the laser.

In conclusion, the present invention includes several modes of measurements, potentially resulting in different types of signature. It is therefore possible, for the same sequence, to accumulate several different signatures whose information may overlap and be complementary.

2) Stiffness of the Single Strands

In the same spirit, the present invention includes the modification of the stiffness of the single strands (which are in series in the measurement) by introducing, in the measuring buffer, particular molecules known to modify the stiffness of the single strands.

In particular, there are numerous proteins which have an affinity for the single strands, such as recA or SSBP (Single Strand Binding Protein), and which can increase the stiffness of the single strands. Likewise, oligonucleotides (for example a random sequence population) may also be used.

Other Experimental Conditions Which can be Envisaged

It may be useful to vary the experimental conditions in order to obtain different signatures on the same molecule. Thus, it is possible to vary the temperature and/or modify the buffer used. In particular, some specific buffers may be advantageously used in order to have an action on the stability of the pairings between bases (for example, Rees, 1993).

Modification of the Duplex or of the Single Strands

It is possible to induce particular marks, or imprints, at certain points of the signature. These are obtained by opening a molecule modified by addition of reagent. The term "reagent" is understood here to mean any molecule capable of establishing a specific interaction with part of the duplex, whether it is open, closed or both open over some parts and closed over others. The modification of the duplex or of the single strands is advantageously chosen so as to locally or substantially modify the force for separating the strands, which may even extend to complete blocking of the opening.

Without as a result being limited thereto, a few examples are given below with:

A)
the introduction of a stronger bond into one or more specific zones of the sequence; this leads, in the signature, to one or more characteristic rises, when the mean opening point reaches these zones;
the introduction of one or more proteins characterized in that they are capable of specifically binding to the duplex, for example to some sequences (such as a methylation enzyme) or alternatively to some structures (such as the binding to a mismatch, with the Mut protein, for example); such a binding can also be used to position a particular reagent (attached to a protein) making it possible to induce an inter-strand "cross link" with a photoactivable group for example;
the introduction of a strengthened inter-strand bond, for example by formation of a triple helix (with a sequence of oligonucleotides or of their analogs); such a bond may also be used to position a particular reagent (attached to the oligo) making it possible to induce an inter-strand "cross link", with a photoactivable group for example;
the buffer used and/or the choice of the temperature can also substantially modify the force necessary to unpair, respectively re-pair, the duplex.

B)
additional molecules can be caused to interact with the single strands of the partially open nucleic acid molecule, characterized in that they preferably bind to at least one specific site on a single strand; during the reclosing and/or reopening, the signal of this signature is then modified.

Uses of the Signatures

One or more signatures, with imprint or otherwise, corresponding to a given duplex, may be compared with references, consisting either of one or more measurements on another duplex, or with numerical calculations, or a combination of both.

It is thus possible to detect and locate the absence or the presence of one or more of the following parameters given by way of example:

homology
translocation,
deletion,
amplification,
homologous repeat regions,
zone of partial pairing,
specific unit of the sequence,
difference,
mutation,
contigation,
a particular region, identifiable by its GC content
a CpG island.

This method constitutes a sequencing aid. It also allows the analysis and the comparison of the genomic differences among various patients or various DNA samples to be tested.

The invention finally relates to a diagnostic kit intended for carrying out the claimed method and which is described below.

The diagnostic kit is characterized in that it comprises one or more of the following components:

at least one spacer arm,
at least one spacer arm cassette molecular construct,
at least one joining oligonucleotide,
at least one hairpin-shaped oligonucleotide,
at least one restriction enzyme,
at least one molecular construct intended to attach the strands of the duplex to be opened to components of the apparatus for measuring force,
a support which is attachable to the functionalized end of the spacer arm,
at least one well,
at least one slide,
at least one type of functionalized and advantageously magnetizable beads intended to be attached to a functionalized component of the duplex to be opened,
at least one magnet,
at least one buffer,
at least one ligation enzyme,
at least one ligation buffer, at least one column for separation by centrifugation.

FIG. 1 illustrates, on one example, the principle of the measurement of force. A double-stranded DNA (5) is opened with force. The single strand on one side of the double helix is connected to a solid substrate (microscope coverslip) (3) via a spacer arm (4) and the other single strand is grafted to a microscopic bead (2). The bead is visible under a microscope and makes it possible to locate the molecule. A device for measuring force (for example a flexible needle (1), optical tweezers, and the like) is connected to the chosen bead. The force is measured as a function of the extension of the molecule.

FIGS. 2, A and B, illustrates an example of the molecular construct.

FIG. 3 represents a cross section of the sample. A ring (6) retains a small volume of buffer liquid and the anchoring of the construct takes place on the glass coverslip (7), (a): beads stuck to the surface, (b): examples of beads correctly attached.

FIG. 4 is a schematic view of the experimental setup. The sample is placed on an inverted microscope connected to a video camera. The force detector is a flexible glass needle (8) mounted on a micromanipulator. Once the lever (attached at its base) is attached, at its flexible end, to a molecular construct, the well is moved sideways and the corresponding deflection of the end of the lever is measured on the video. A computer (PC) is used to control the movement and acquire the deflection data.

Figure 7A:
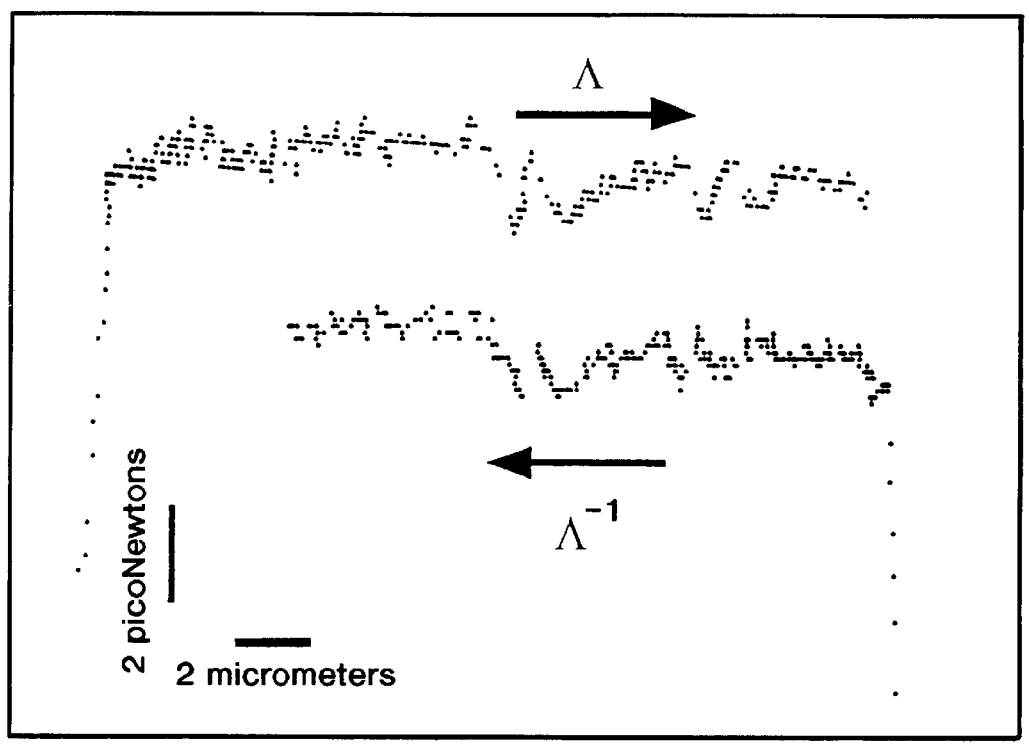
Figure 7B:
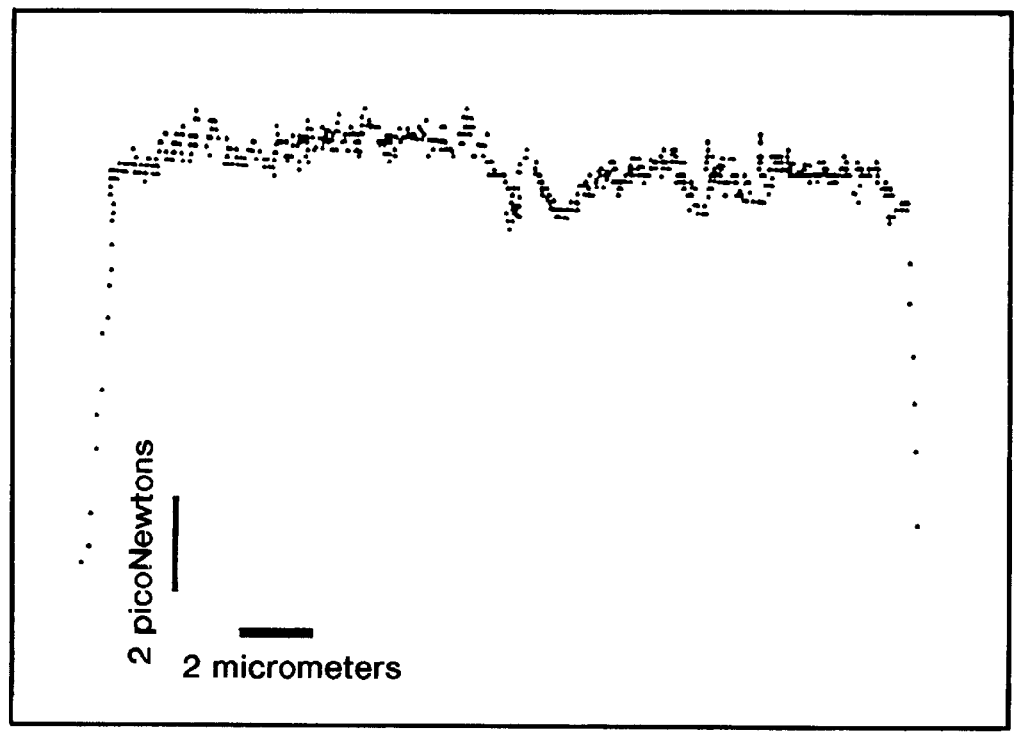

FIG. 7 illustrates the comparison of the forces as a function of the signal of the end-to-end distance of the molecular construct $\Lambda$ and $\Lambda^{-1}$, (defined later). The speed of translation used in these measurements of opening is about $\Lambda$=0.06 $\mu$ms−1. In FIG. 7B, the two measurements are directly superposable.

Figure 8A:
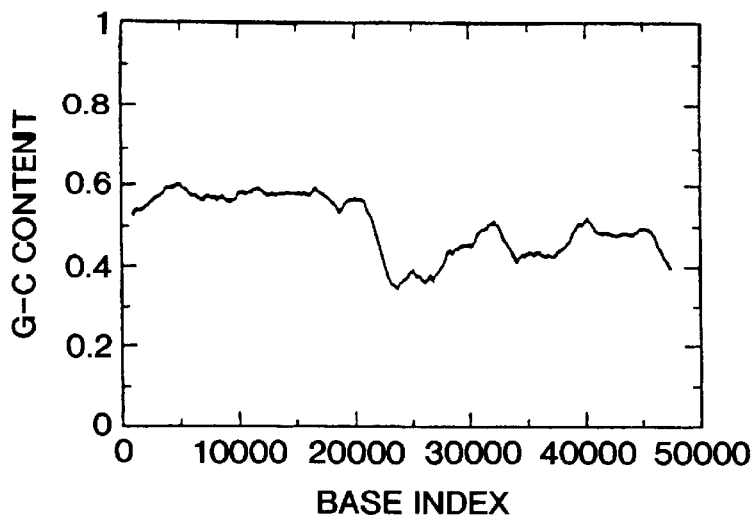
Figure 8B:
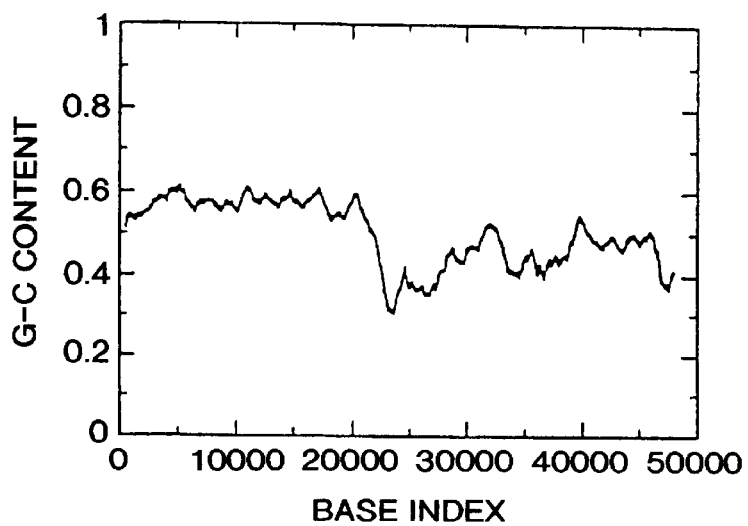
Figure 8C:
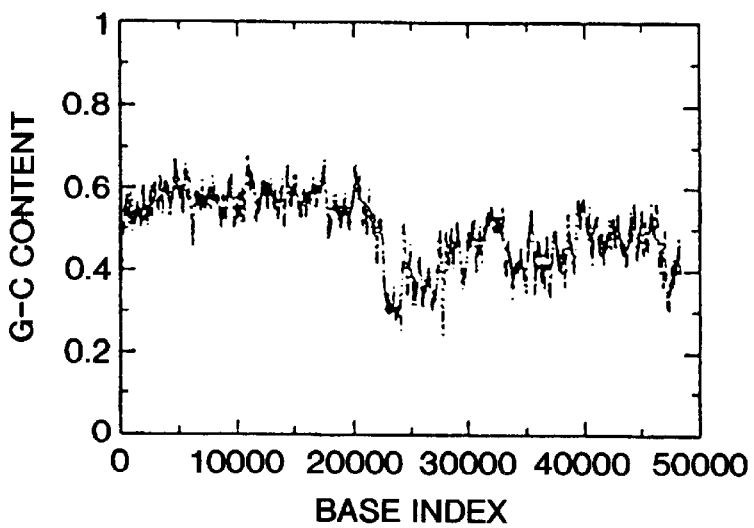

FIG. 8 illustrates the mean GC content along the $\lambda$ phage molecule. An averaging is performed on 200 bases (FIG. 8C), on 1000 bases (FIG. 8B) and on 2000 bases (FIG. 8A).

Figure 9A:
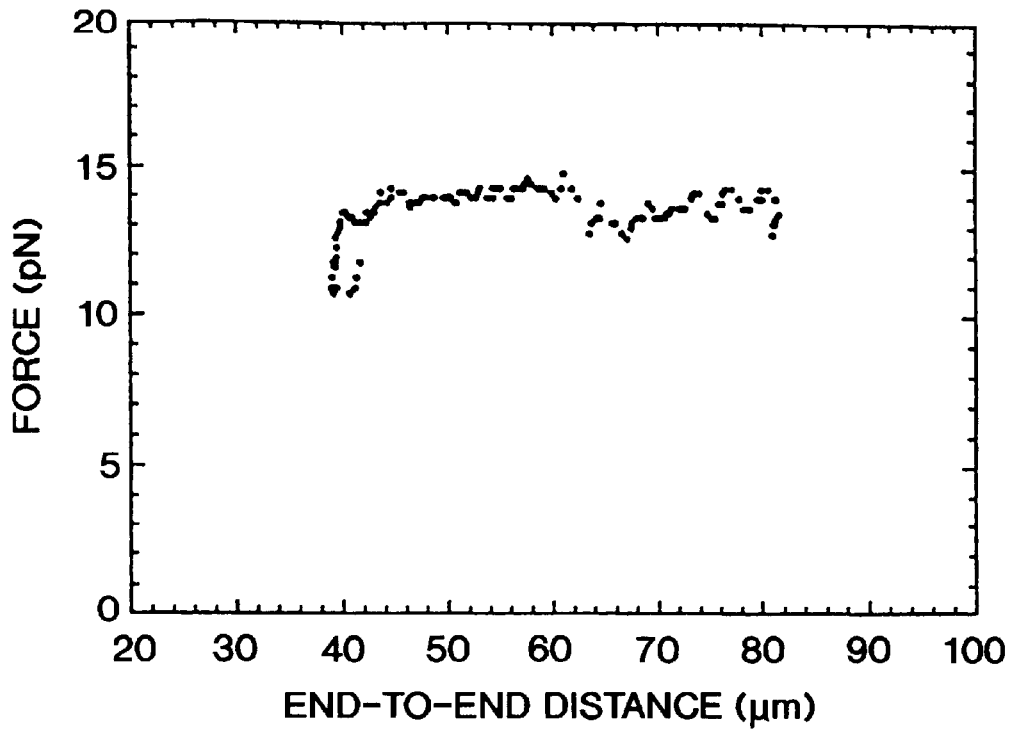
Figure 9B:
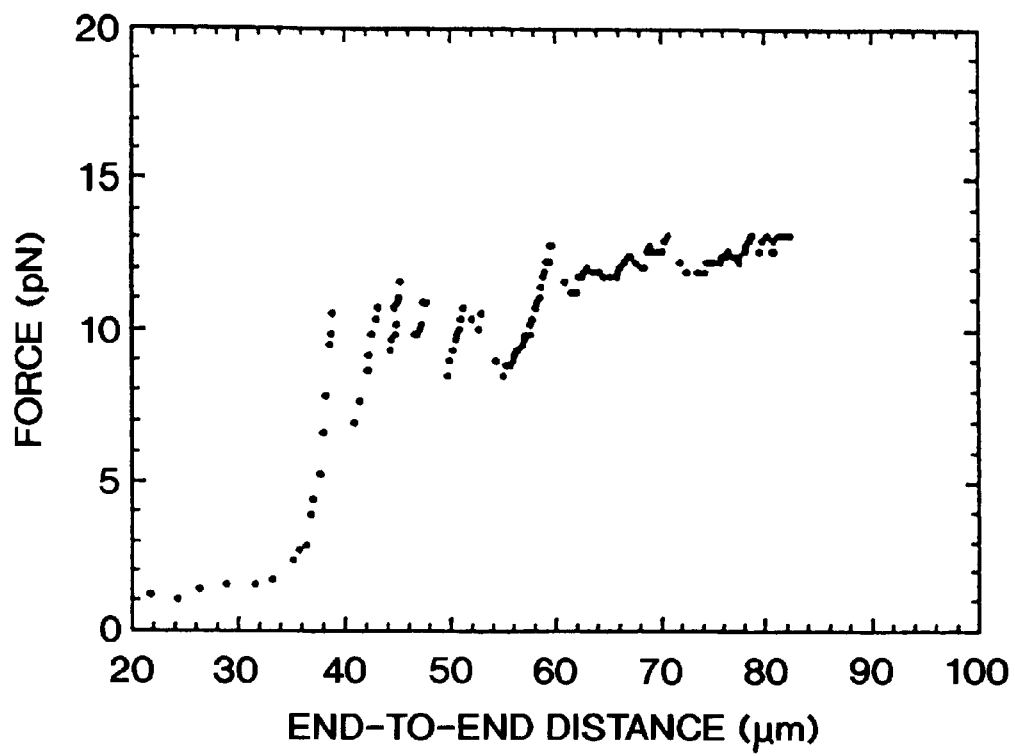

FIG. 9 illustrates the comparison of the force measured during the opening (FIG. 9A) and the closing (FIG. 9B) of the same molecule at the same translational speed.

Figure 10:
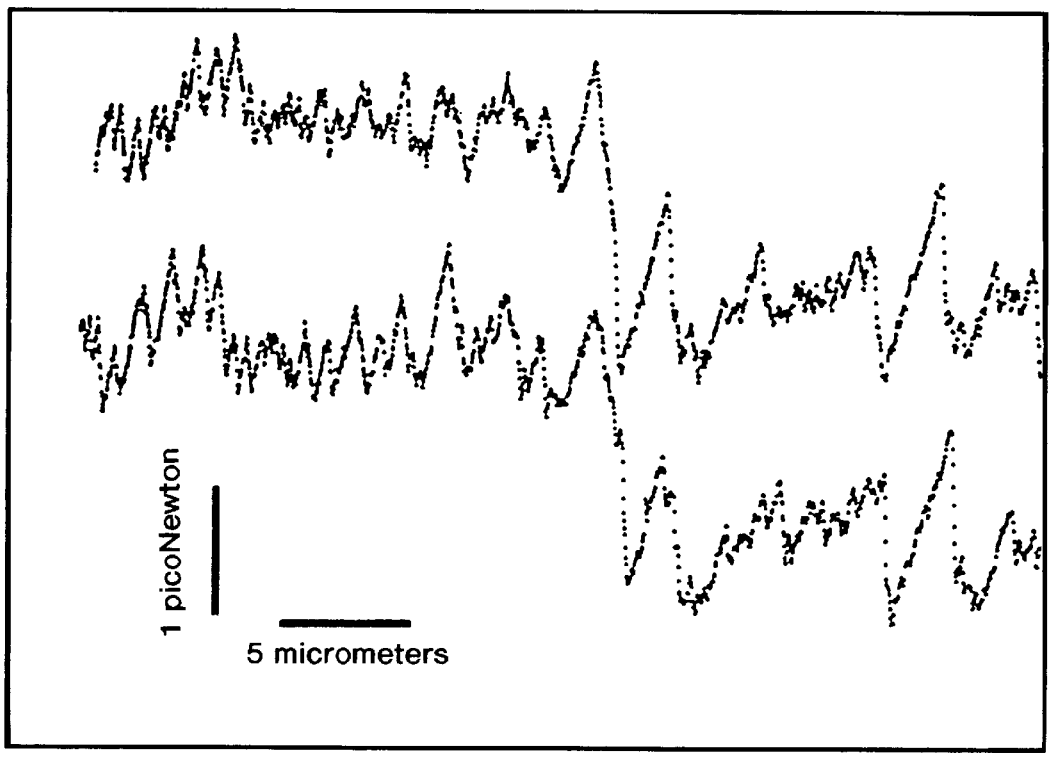

FIG. 10 shows the reproducibility of the force signal for two measurements, at different moments, on the same molecule and at the same speed of movement (160 nm/sec).

Figure 11:
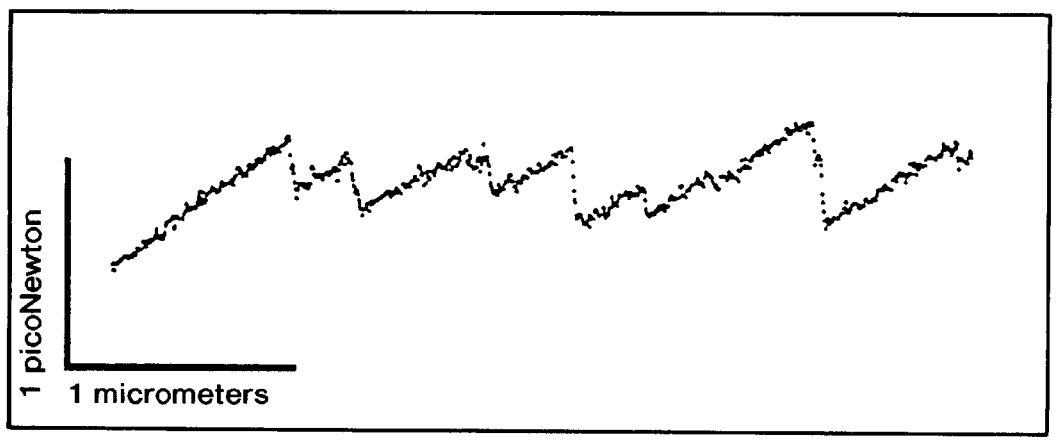

FIG. 11 shows the details of a force signal at low speed of movement (40 nm/sec), where the serrated structure can be clearly seen.

Figure 12A:
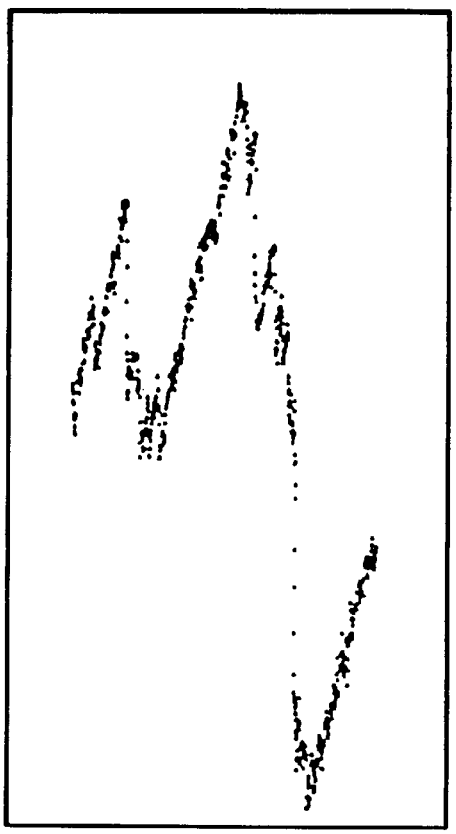
Figure 12B:

FIG. 12 makes it possible to compare one detail of the measurement (peak-peak amplitude of about 2 pN; GC hollow in the middle of the $\lambda$ opening) with the GC content (sliding mean over 500 bases ) represented for the corresponding piece between the base indices from 15,000 to 25,000.

Figure 13:
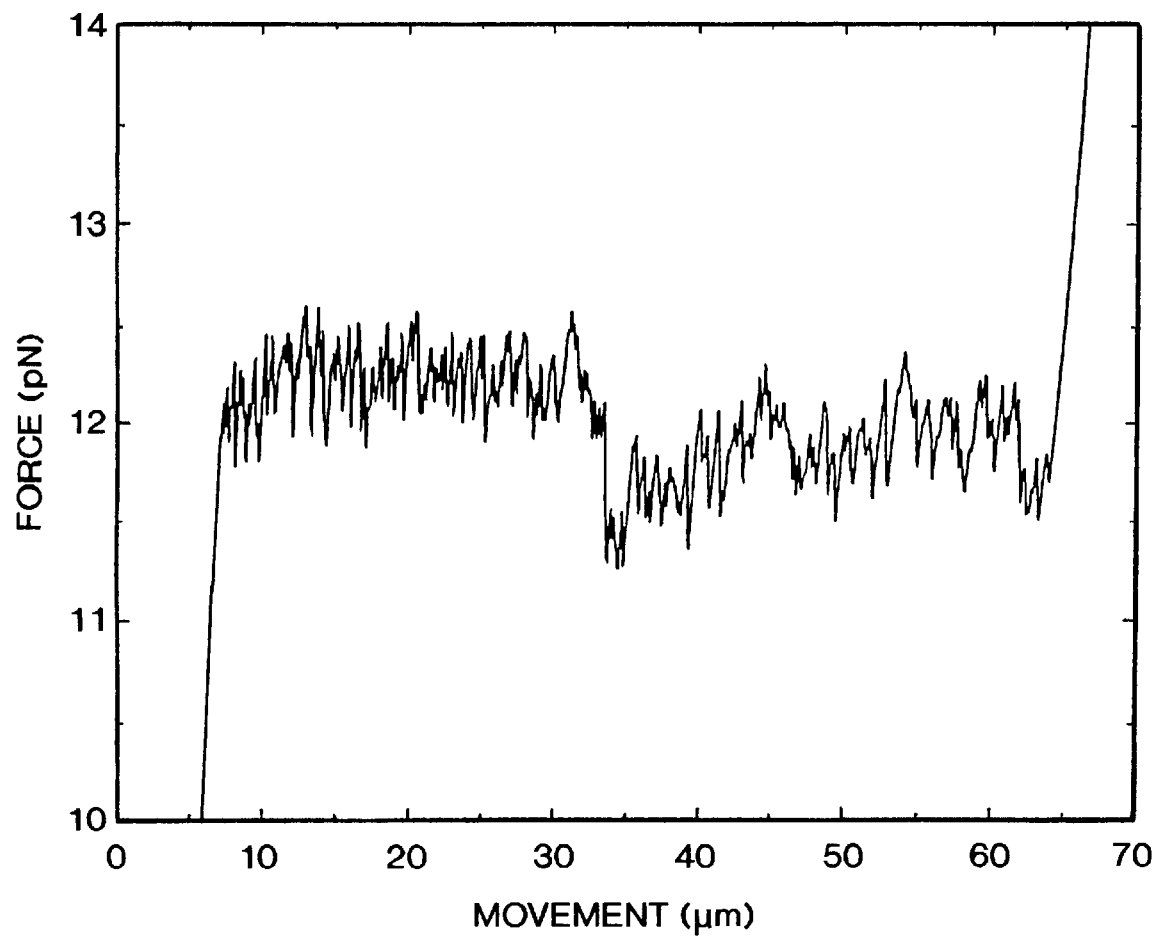

FIG. 13 illustrates a numerical calculation of the force signal for a $\lambda$ phage DNA molecule. The horizontal axis is shifted in relation to the experimental measurements because the spacer arm is not included in the theoretical description.

Figure 14:
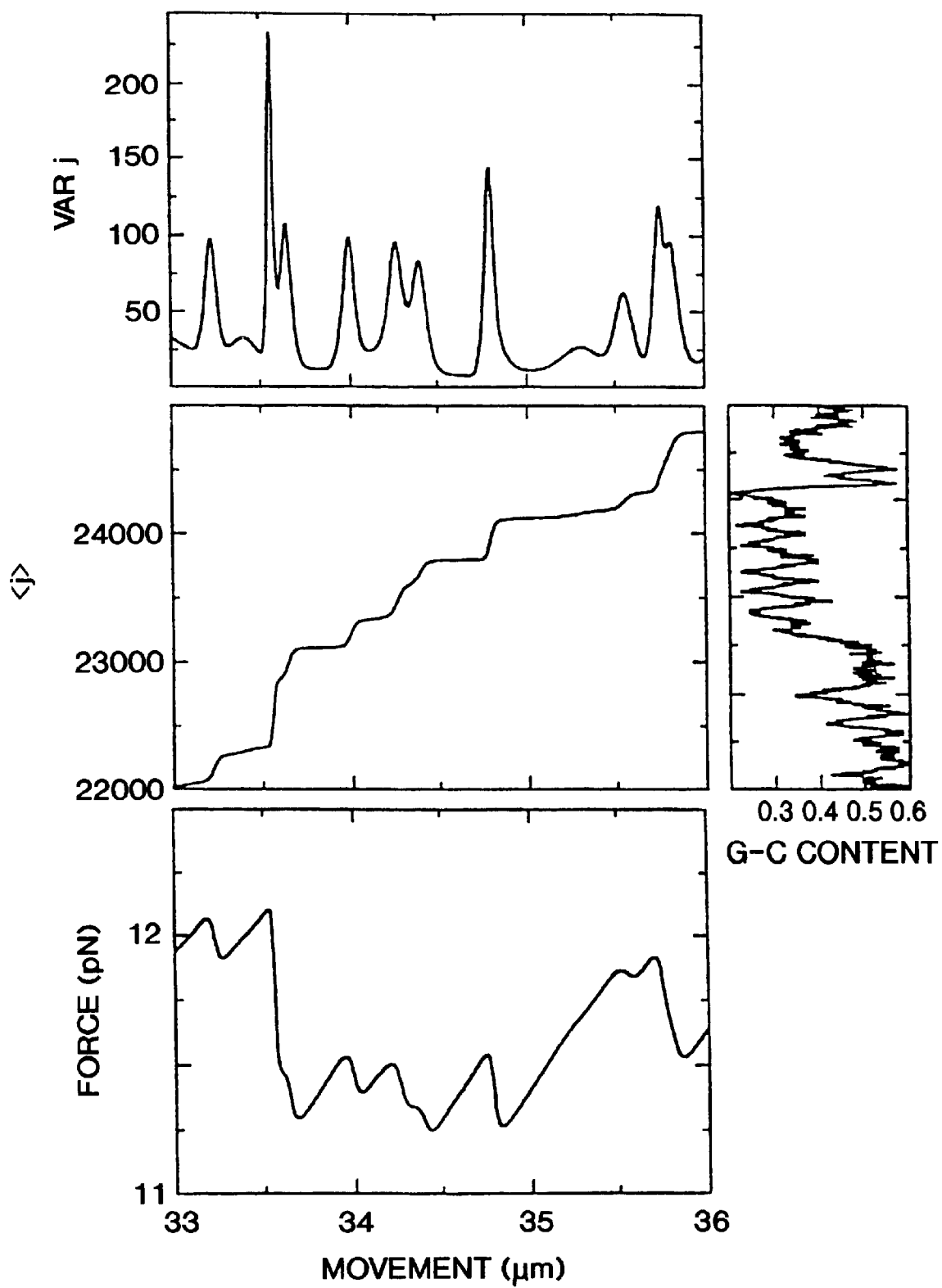

FIG. 14 illustrates a set of theoretical results on the physics of the opening. From the bottom to the top, the deflection force, the mean number <j> of open base pairs, and the variance of j are presented as a function of the movement of the sample (in micrometers) which controls the opening process. The mean GC content corresponding to the open sequence is plotted on the right (sliding mean over 100 bases).

By the choice of the common axes, the figure makes it possible to link the structures in the GC content, to the deflection force, to <j> and to the variance of j (and vice versa).

Figure 15:
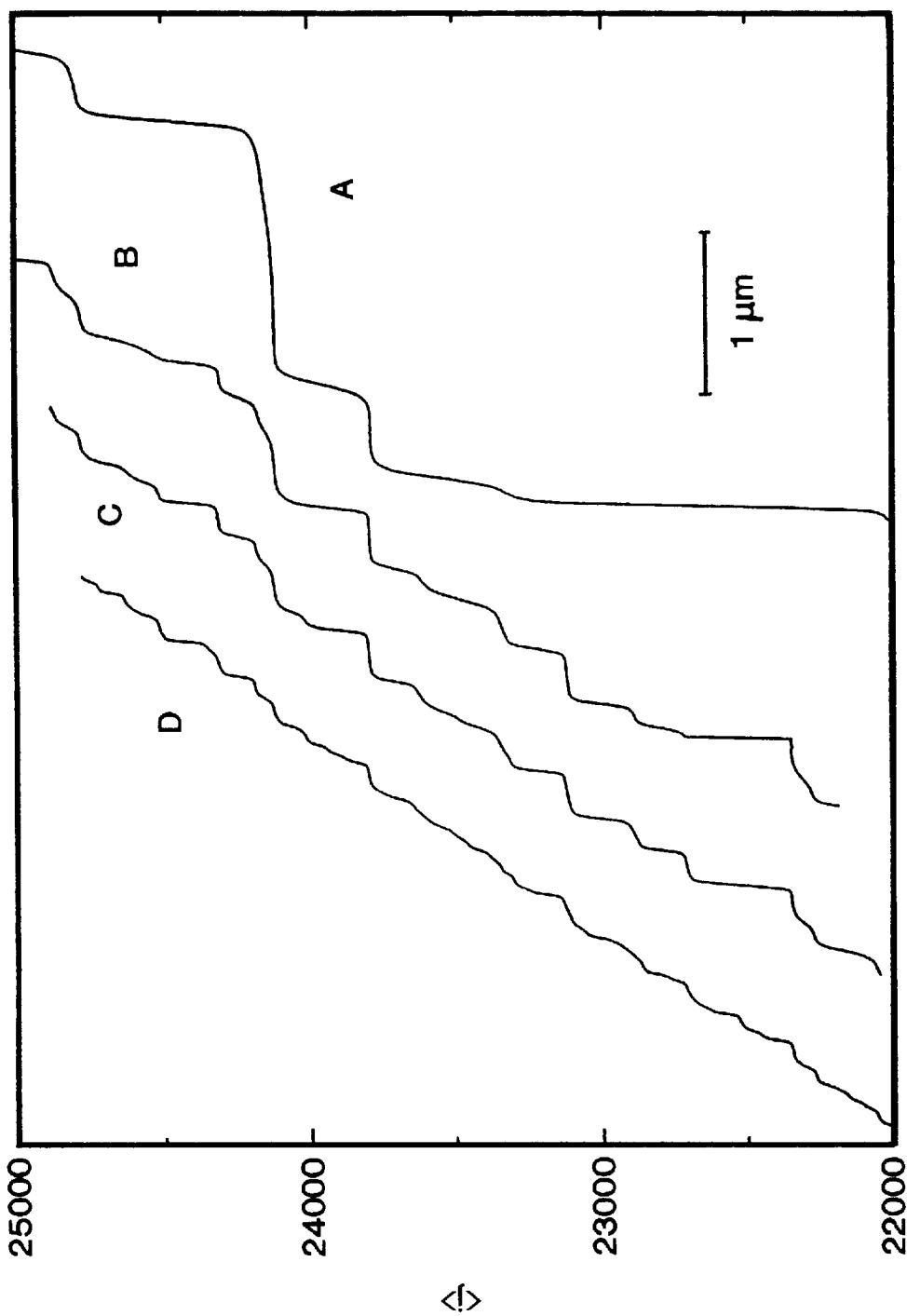

FIG. 15 illustrates the effects of the stiffness of the lever and of the single strands. The mean number <j> of open pairs have been plotted as a function of the movement (movement scale given by the horizontal bar). In these calculations, the stiffness of the lever $k_{lev}$ is four times smaller (curve A), two times greater (curves B and C), or ten times greater (curve D) than the stiffness of the lever used in the experiments. For curves C and D, it has been assumed that the length of each of the two single strands is reduced by 20,000 bases, which makes it possible to observe the influence of the elasticity of the single strands.

Figure 16:
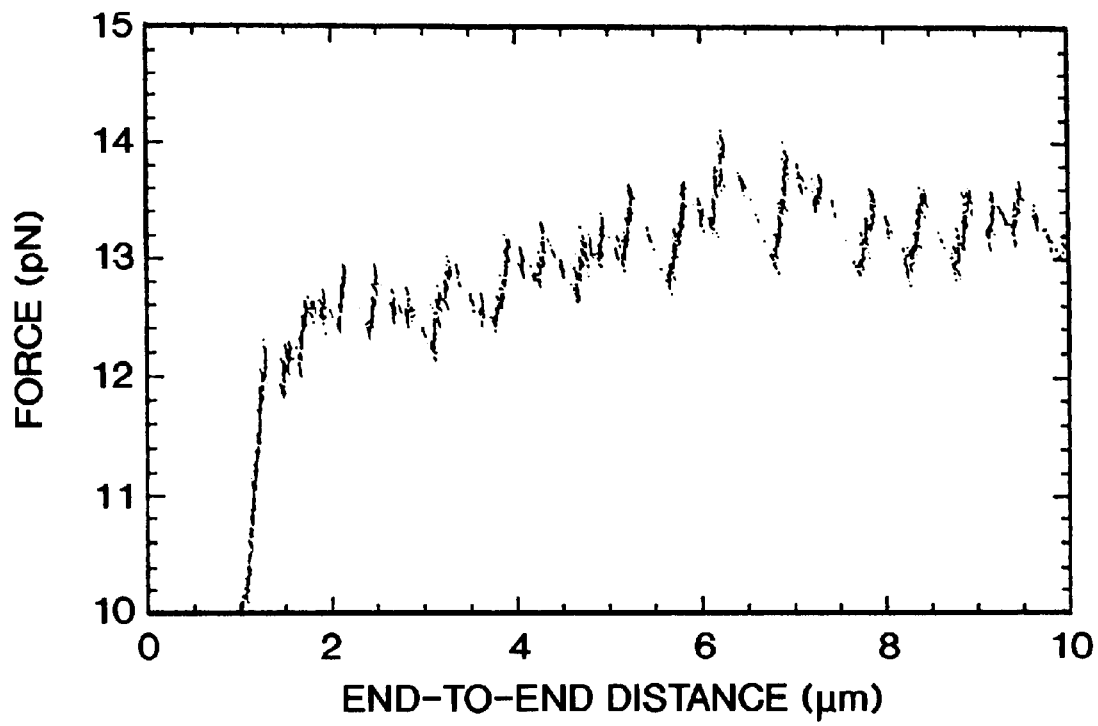

FIG. 16 illustrates a measurement of force during the opening on the construct $\Lambda$, obtained with a lever having a stiffness of about 2.5 pN/$\mu$m. The points are experimentally obtained by the analysis III, described elsewhere. The force expressed in picoNewtons is plotted as a function of the end-to-end distance expressed in micrometers.

Figure 17:
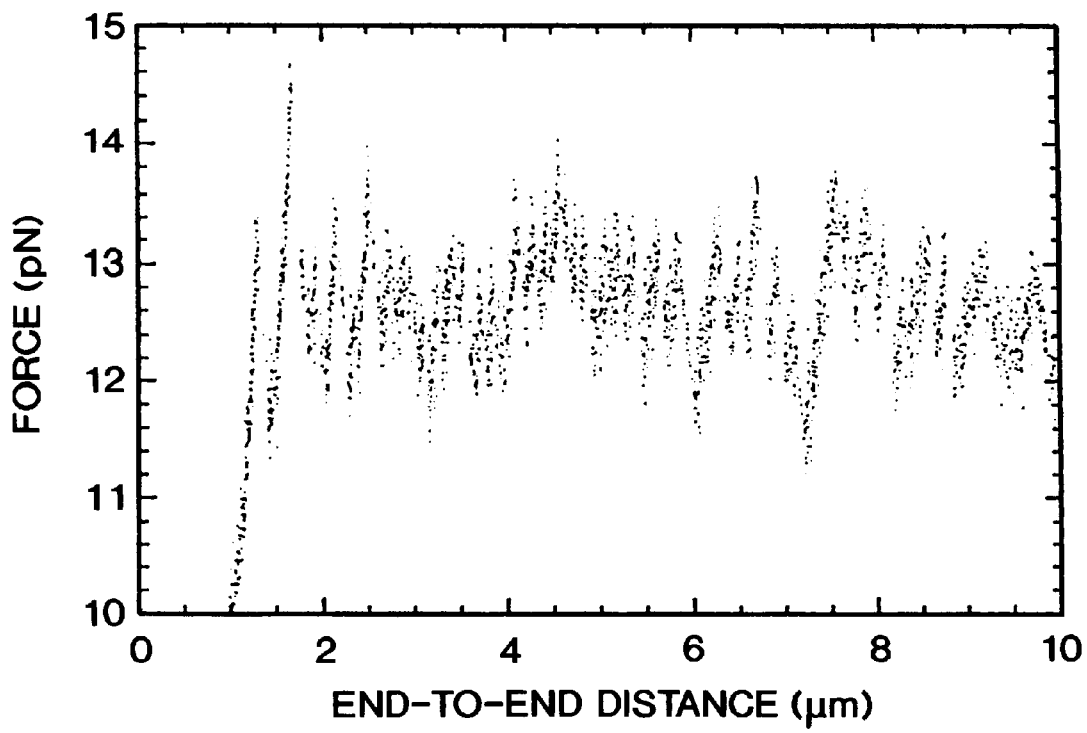

FIG. 17 illustrates a measurement of force during the opening on the construct $\Lambda$, obtained at the same opening speed as for FIG. 16, and by the same system of measurement but with a lever having a stiffness of about 19 pN/$\mu$m. The force expressed in picoNewtons was plotted as a function of the end-to-end distance expressed micrometers.

Figure 18:
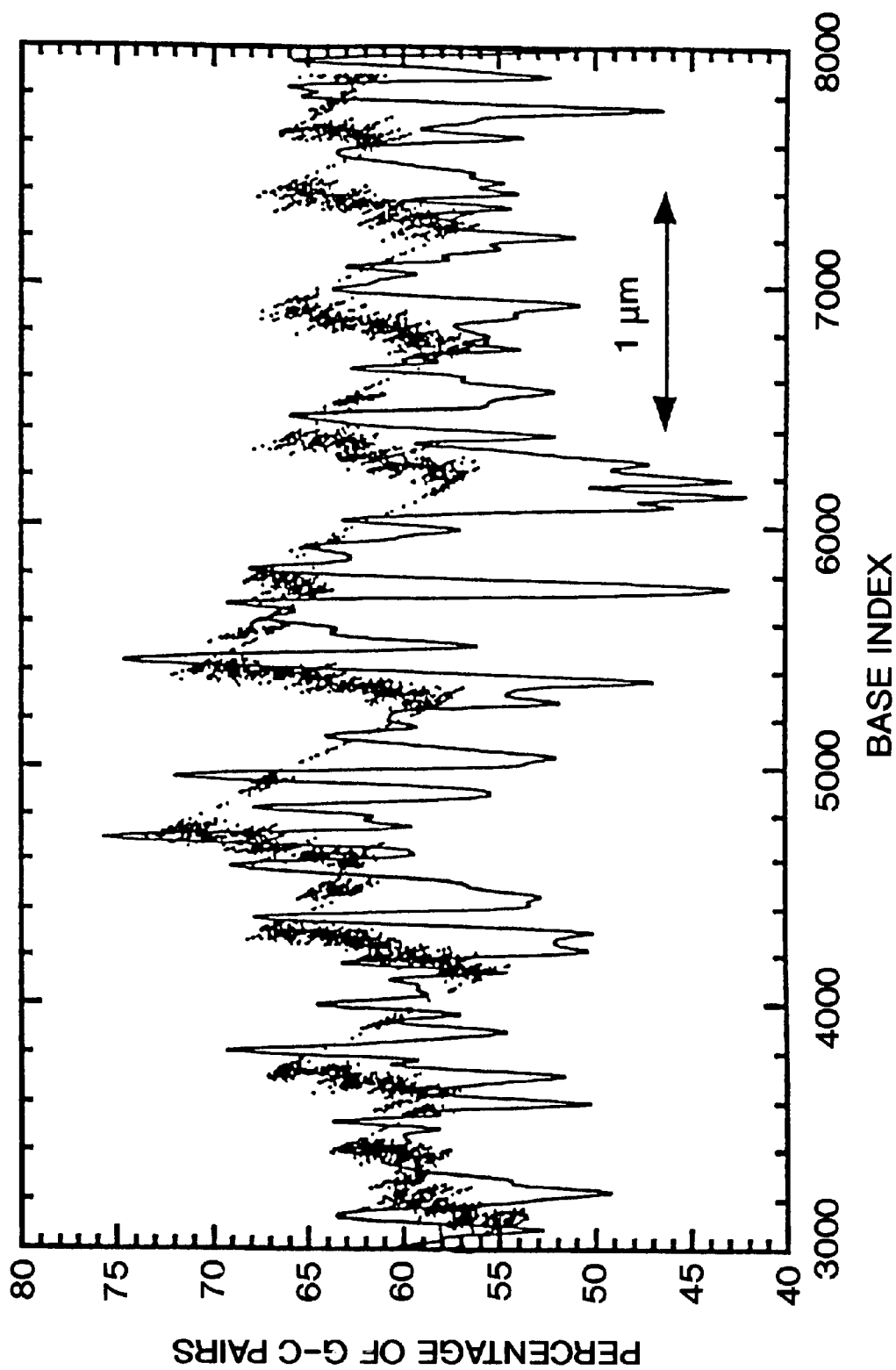

FIG. 18 illustrates a superposition between the force signal obtained during the opening, and the mean content of G or C base along a given segment of the sequence (from 3000 to 8000); the mean is a Gaussian mean, having a total characteristic width at 1/e of 50 bases. The curve give the mean is plotted with a continuous line. The experimental curve is plotted with discrete points.

PRACTICAL EXEMPLARY EMBODIMENT

The details of the preparation and measurement of signature according to the present invention on lambda phage DNA are described here with no limitation being implied, and as an example.

Figure 1:
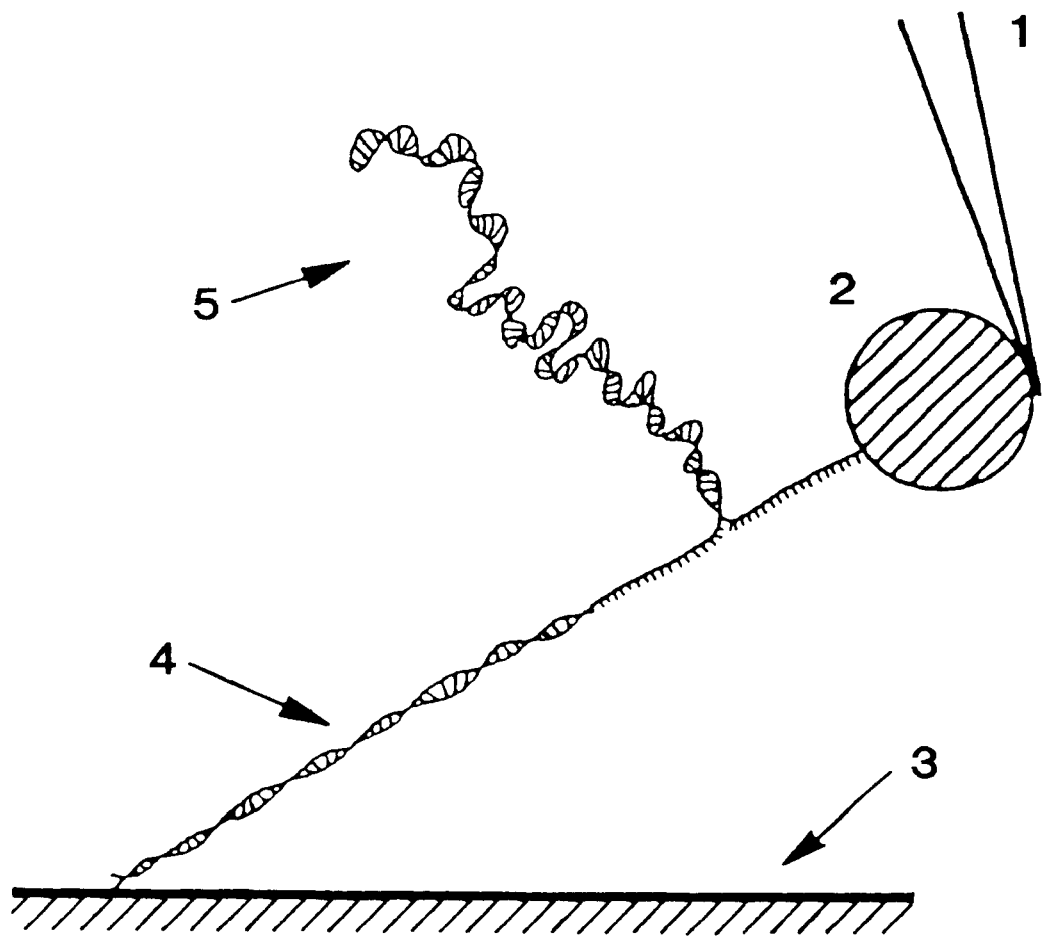
Figure 2A:
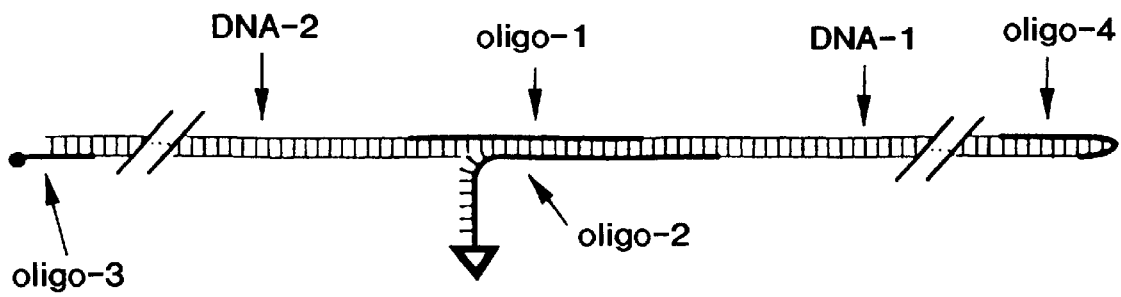
Figure 2B:
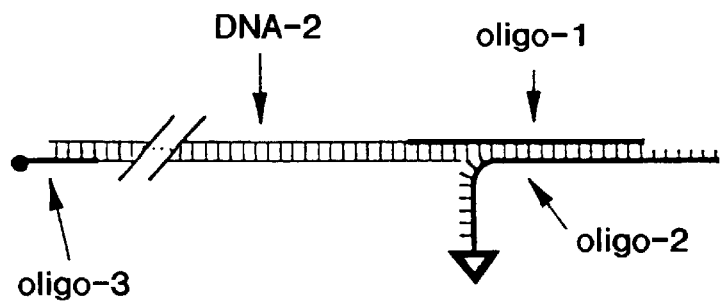
Figure 3:
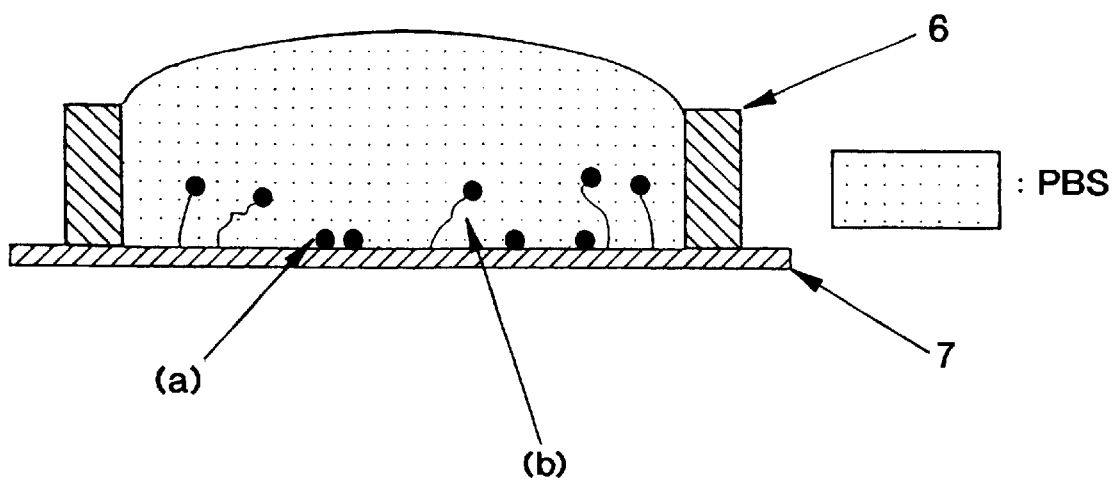
Figure 4:
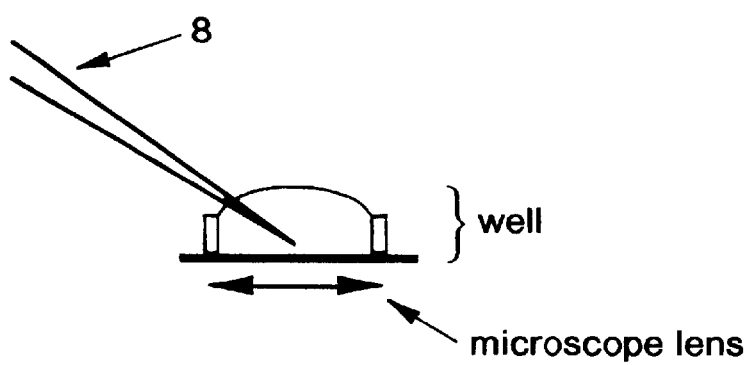

Construct (FIGS. 1 and 2)

Oligo 1 is a connecting component between DNA 1 ($\lambda$ phage DNA intended to be opened) and DNA 2 ($\lambda$ phage DNA which serves as spacer arm). Oligo 2, a connecting component, is 3' biotinylated, which serves for the attachment to a bead. Oligo 3 is 3' dig functionalized and serves for the attachment to the surface. Oligo 4 is a cohesive mini-hairpin.

The sequences chosen by way of example are the following:

Oligo 1 (SEQ ID NO.1)
5' Agg TCg CCg CCC AAg ggA CTA CgA gAT Tg 3'
Oligo 2 (SEQ ID NO.2) (3' biotin functionalized)
5' Agg TCg CCg CCC CAA TCT CgT AgT CCC AAA AAA TCA gCA gTA AC biotin 3'
Oligo 3 (SEQ ID NO.3) (3' dig functionalized)
5' ggg Cgg CgA CCT dig 3'
Oligo 4 (SEQ ID NO.4) (cohesive mini-hairpin)
5' ggg Cgg CgA CCT AgC gAA AgC T 3'

The preparation is carried out in the following manner, for example from 10 $\mu$g of DNA 1 and 10 $\mu$g of DNA 2:

The buffer used during the fusions below is the ligation buffer without ATP (Pharmacia). The reaction volumes are typically from 20 to 60 µl.

1) Fusion (55° C., 1 hour) and ligation (T4 ligase (Pharmacia) 0.2 Weiss units, 1 hour, 16° C.) of:
   DNA2+oligo 3, that is to say preparation A (molar ratio: 1/10);
   DNA1+oligo 4, that is to say preparation B (molar ratio: 1/10).

1bis) Heat-inactivation of ligase.

2) Fusion (55° C., 1 hour), ligation (T4 ligase (Pharmacia) 0.2 Weiss units, 1 hour, 16° C.), heat-inactivation of ligase and purification of:
   preparation A+oligo 1, that is to say preparation C (molar ratio: 1/20);
   preparation B+oligo 2, that is to say preparation D (molar ratio: 1/20).

3) Fusion (40° C., 1 hour, then slow cooling), ligation (T4 ligase (Pharmacia) 0.2 Weiss units, 2 hours, 16° C.), heat-inactivation of ligase and purification of:
   preparations C and D, adding PEG (10%) in order to promote the reaction, that is to say preparation E.

Typically, 2 ng of construct are used per experiment.

The purification steps are carried out using Amicon-100 filtration columns.

Sample

The experiments are carried out in a liquid (buffer of controlled pH and with a given salt concentration; PBS, 10 mM phosphate, 150 mM $Na^+$, pH=7.0, is for example used). A plastic ring is stuck with paraffin to the microscope slide and makes it possible to maintain a small volume of buffer above the glass surface. This constitutes a well in which the measurements will be carried out. The functionalized glass surface (bottom of the well) will anchor the molecular construct. The particles are then added and a number of them will become attached. The well is placed on an inverted microscope and the measurement of the forces is carried out using a flexible microneedle, introduced into the liquid through the free part of the meniscus.

Naturally, an optical trap (Svoboda et al., 1993; Finer et al., 1994; Yin et al., 1996) may be advantageously used as force sensor, in place of a microneedle.

Finally, care should be taken to avoid positively charged surfaces so as to avoid undesirable adsorption of DNA.

1) Support No. 2: The Particles are Beads

The beads used are paramagnetic, commercially available Dyna beads (diameter 2.9 µm). These beads are coated with streptavidin and an additional treatment with an acetylation agent (NHS acetate) is applied to them.

2) Support No. 1: Microscope Coverslips and Their Preparation

In the preparation steps, a very small reaction volume, about 10 µl, is created by the use of a small circular disk of thin glass (diameter 12 mm) which is placed inside the plastic ring of the well and serves as cover. When it is necessary to perform a chemistry by the liquid route, the liquid, about 10 µl, is first added to the well and the disk then placed on top adheres by capillarity. The liquid becomes confined between the bottom of the well, on the one hand, and the circular coverslip, on the other hand; the liquid is distributed over the entire surface with an approximately uniform thickness of about 10 µm. The incubation is then carried out in the covered well. For the next step, 300 to 400 µl of buffer are added inside the ring of the well, the glass disk floats outside of the base of the well and is easily removed with forceps. The excess buffer is removed by tilting the well over an absorbent paper.

Microscope glass coverslips are prepared on which negatively charged, linear polymers are grafted (random polymerization of maleic acid and of acrylamide on the vinyl silanized coverslips, which creates a negatively charged and very hydrophilic surface). This allows subsequent functionalization with the antidig.

By way of example, it is possible to use, for the silanization, a trichlorosilane, with an intermediate chain composed of 5 to 20 carbons, ending with a vinyl group. The glass surfaces are introduced into a sealed chamber, provided with an access trap and with inlet and outlet tubes, provided with taps. This chamber contains a tube which generates UV, consisting of a low-pressure mercury lamp (Heareus trademark) generating UV over a range of wavelength which partially covers the oxygen absorption band. In a first instance (10 minutes), the chamber is flushed with a stream of gaseous oxygen. The taps are then closed and the lamp is switched on for one or more hours. Ozone is created and helps to clean the glass surfaces. After stopping the UV, a gaseous stream is introduced for 5 minutes. It is oxygen which has bubbled through water. The coverslips are rapidly extracted from the chamber and introduced into a hermetically sealed glass chamber in which a few drops of silane have been placed. The silanization occurs by gaseous transfer. After a few hours, the slides are placed in an oven (typically 150° C. for one hour), and then rinsed under a thin jet of water and stored in a cup made of aluminium sheet for example.

Using the coverslips, wells are manufactured as described above. In the wells, there is introduced a small volume of a mixture consisting of:
   acrylamide,
   maleic acid neutralized pH 7 at the time of use,
   deoxygenated water,
   persulfate (initiator),
   TEMED (initiator).

The acrylamide/maleic acid ratio is chosen in the range 10/1 to 5/1.

The polymerization is carried out in the wells, protected by their cover.

This procedure allows the production of an electronegative and hydrophilic matrix consisting here of the acidic groups (derived from maleic acid), incorporated into the long polymers derived from the polymerization of acrylamide, which are themselves anchored on the surface.

The highly electronegative character makes it possible to effectively combat the adsorption of DNA, a negatively charged polyelectrolyte.

Persons skilled in the art can naturally adapt this particular design of electronegative matrix to other systems. By way of example, there may also be mentioned a matrix obtained by attachment of dextran, followed by a step for converting the sugars in order to obtain acidic groups.

An electronegative matrix is characterized in that it consists of polymers having an overall electronegative and hydrophilic character, attached to a support; the polymers may be random and/or branched, but on average consist of the assembly of at least one type of monomer. The typical size of the polymers, expressed as number of monomers incorporated, is at least two, preferably between 10 and 1000 and even capable of ranging up to one million, and the final matrix exhibits randomly or uniformly a density of —COOH groups at least greater than 1/1000 and preferably of between 1/20 and 1/1.

The antidig (polyclonal, Boehringer Mannheim) is coupled, via $NH_2$ groups to part of the COOH matrix using the EDC-NHS or EDC-NHSS techniques.

After removing the cover and rinsing, a thin film of buffer remains on the hydrophilic surface of the treated glass surface. It is then possible to carry out the other coupling operations.

The coupling of the antidig is carried out in the following manner:

10 minutes of EDC-NHSS incubation (in water) (EDC= 1-ethyl-3-(3-dimethylaminopropyl)carbodiimide in hydrochloride form, NHSS=sulfo-NHS (N-hydroxysulfosuccinimide));

10 seconds of rinsing under a thin jet of water;

10 minutes of coupling with the antidig in PBS;

10 minutes of deactivation with 1 M glycine, pH 8, in order to allow recovery of the COOH groups from the EDC-NHSS residual activated sites;

rinsing.

The antidig surfaces with an antimicrobial agent (0.02% $NaN_3$) and protected by a coverslip are placed in a bag with a humid atmosphere and may be stored for weeks in a refrigerator. On carrying out the experiments, the wells coated with antidig are rinsed with PBS, incubated with a dilution of molecular construct in PBS (typically 1 ng of construct in 10 $\mu$l) for 30 minutes. The dilutions and incubation buffers can naturally be adapted. Next, an excess of buffer is added and the streptavidin-coated beads are introduced. They sediment and react with the molecular construct at the surface of the microscope slide. After typically one hour of incubation, a large portion of the nonattached beads are removed by rapidly dipping a small magnet into the well, the magnet attracts and sticks to the free particles. Next, the step of selecting the beads described above and which uses the presence of a spacer arm is carried out.

Typically, from 0 to 50 attached beads are observed in a field of view, under the microscope with a 20× lens. In the same field, typically a fraction varying from $\frac{1}{10}$ to $\frac{3}{4}$ of the beads may be stuck or adsorbed.

Naturally, surfaces other than glass, in particular polymeric materials, may be used, both for the bottom of the well and for the cover. The latter may also be made with other materials, a metal or a ceramic by way of nonlimiting example.

The Force Lever: Flexible Glass Microneedle

A commercial apparatus for drawing pipettes is used. Microneedles are prepared (whose typical dimensions are: diameter: 1 mm, diameter of the end: 1 $\mu$m and length 1 cm). The stiffness varies as a function of the needles and is calibrated (see later). The needles are chemically biotinilated as follows:

washing with sulfochromic mixture;

silanization (with a silane ending with a primary amine);

reaction with NHS-LC-biotin (Boehringer) (which reacts the primary amines).

The treated lever rapidly adheres to the streptavidin-coated microbeads simply by touching them. The measurements of force can be carried out immediately. After the measurement, the microbeads may be separated by a mechanical shock on the lever, or by using a meniscus effect simply by lifting the lever out of the well and then by reimmersing it in the liquid.

Measurement of the Forces

The sample is placed on an inverted microscope comprising a high-magnification lens (Zeiss Achroplan, oil immersion, ×100, N.A. 1.25). The image of the bead and of the flexible end of the lever is obtained by a video camera. A piezo translation stage allows a precise sideways movement of the sample in relation to the fixed base of the force lever. (Kinematic inversion can of course be envisaged).

This movement is measured with a resolution which is better than the micron using an inductive sensor. A computer makes it possible to link the information on the movement of the sample and the deflection of the lever which is recorded by a video camera (the video image is captured by a numeric acquisition system). The forces involved in the experiments for opening of the DNA are of a few tens of PicoNewtons, which typically correspond to a movement of the end of the lever of a few tens of microns.

Two types of method were used to obtain these deflection data. In the only slightly resolved mode (called Analysis I), the determination of the deflection is carried out at a resolution of about 0.2 $\mu$m, which corresponds to that of pixels (numerical acquisition of the image). A second, more sensitive mode was used (called Analysis II). Using the fact that the beads exhibit a highly contrasted image (white in the center, black on their periphery), the method chosen is the following: a single video line of the image is chosen and selected so as to cover a section of the bead; the video line exhibits a gray background structure on which the high and localized black-white-black modulation which corresponds to the bead is superposed. A numerical method then makes possible, with a subpixel resolution, the interpolation of the position of the center of the bead. It is thus possible, starting with the video recording of the movements of the bead stuck to the lever, to go back to the deflection during the experiment, with a resolution of the order of about twenty nanometers (Analysis II).

The stage affording piezoelectric movement allows arbitrary sequences of movement as a function of time.

Calibration of the Stiffness of the Levers

The microneedle for calibrating is first biotinilated as described above. A paramagnetic bead (Dyna) is attached to the end of the microneedle in a well (without DNA) filled with buffer. A small magnet is brought closer to within a few tens or hundreds of microns, and the deflection of the end of the lever as a function of the distance between the bead and the magnet is measured. The magnet is then moved apart to a position which corresponds to a small deflection. The bead is then mechanically detached from the flexible lever using a second, stiffer microneedle controlled by micromanipulation. The bead then moves rapidly toward the magnet.

Using a stroboscopic illumination, the position is located as a function of the time of the bead during the acceleration toward the magnet. The speed of the bead as a function of the bead/magnet distance is obtained from video information. The local speed v is proportional to the force on the bead (by the Stokes formula: $F=6\pi\eta Rv$ in which $\eta$ is the viscosity of the buffer and R is the radius of the bead).

From the two sets of measurement (deflection of the lever as a function of bead/magnet distance and speed of the bead as a function of the bead/magnet distance), the relationship between force and deflection is obtained, that is to say the stiffness of the lever. A single lever was used during the various experiments. Its stiffness was estimated at 1.7 pN/micron (with an accuracy of 20%). An independent confirmation of this calibration is the following: occasionally when the molecule refuses to open, a characteristic plateau in the curve extension as a function of the force of the double helix, are then measured (Cluzel et al., 1996; Smith et al., 1996). Using the stiffness of the calibration, the values of the forces obtained for this plateau are compatible with those given in the literature.

Measurements of the Opening of the DNA by Mechanical Forces

Figure 5:
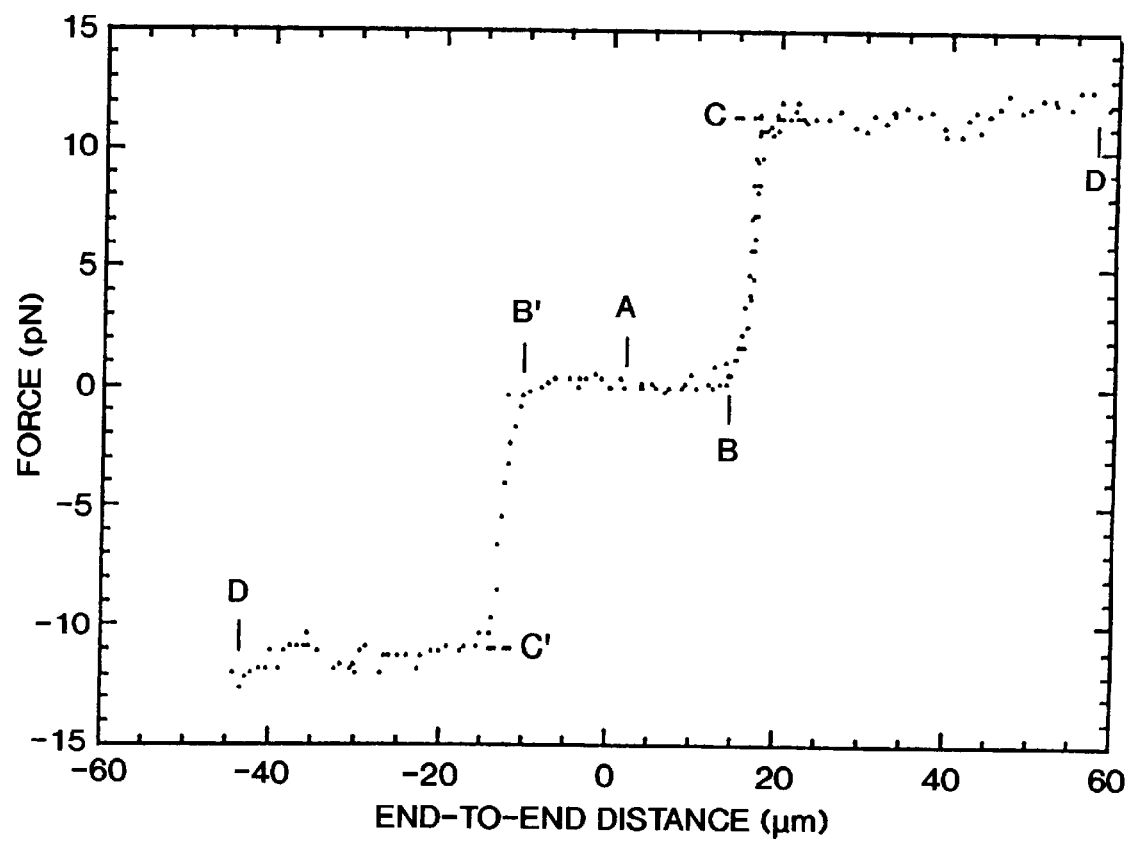
FIG. 5 illustrates the fact that the force (deflection of the lever) is a function of the "end-to-end distance" during the extension of the molecular construct.

A first example of the measurement of force during the opening of the λ phage DNA has been represented in FIG. 5, with the Analysis I. The horizontal axis corresponds to the distance between the two anchorages of the molecular construct (end-to-end distance, defined as the movement of the well measured from the attachment of the lever, subtracted from the deflection of the lever). At point A, at a force zero and at a distance zero, no measurable mechanical force is exerted by the lever on the molecule; through the action of entropic forces, the double-stranded spacer arm of the λ DNA before the attachment of the lever becomes compacted near the point of anchorage (distance equal to zero, identified as the mean position of the bead before the attachment to the lever). Just after the attachment of the bead to the lever, the lever is raised by a few micrometers above the surface in order to avoid solid frictions. By moving the sample sideways in the positive or negative X direction, a measurable deflection appears when the end-to-end distances approach the length of the λ DNA spacer arm (about 16 μm). The segment A-B-C (respectively A'-B'-C') corresponds to the entropic extension of the spacer arm. The regime described by Bustamante et al., (1994) on the extension of a simple DNA double helix is found here.

At point C (respectively C'), a sudden change in the dependence of the force as a function of the distance is observed. A quasi plateau C-D (respectively C'-D') is observed at a force of about 11 to 13 pN. This plateau corresponds to the separation of two strands of the DNA molecule, of which one strand is attached to the long spacer arm of DNA and the second strand to the bead. The distance A–D in FIG. 5 exceeds three times 16 μm, which is expected since the following lengths are involved: the spacer arm of about 16 μm plus twice the length of the stretched singlestranded DNA. At this coarse level of resolution, the opening appears at a practically constant force value.

FIG. 5 was obtained by a rapid cycle of movement. By carrying out the return from D to A, the two strands become re-paired and a new measuring cycle can be performed. During the return, a phenomenon of hysteresis is observed as will be described in FIG. 9.

When the λ molecule is completely open, the force increases and corresponds to the linear extension of the three components in series, the spacer arm and the two single strands linked by the hairpin.

Occasionally, the characteristics of the opening are different:
- a force considerably greater than what is expected is observed just before the opening (which probably corresponds to a partial adsorption of the beads on the double strand); occasionally, the molecules do not open, even for forces greater than 50 pN;
- the curve of end-to-end distance as a function of the force increases although the opening is not complete; this blocking of the opening may be repeated or transient, which may be due to knots or inter-strand bonds.

Finer Analysis of the Force/Distance Curve

Figure 6A:
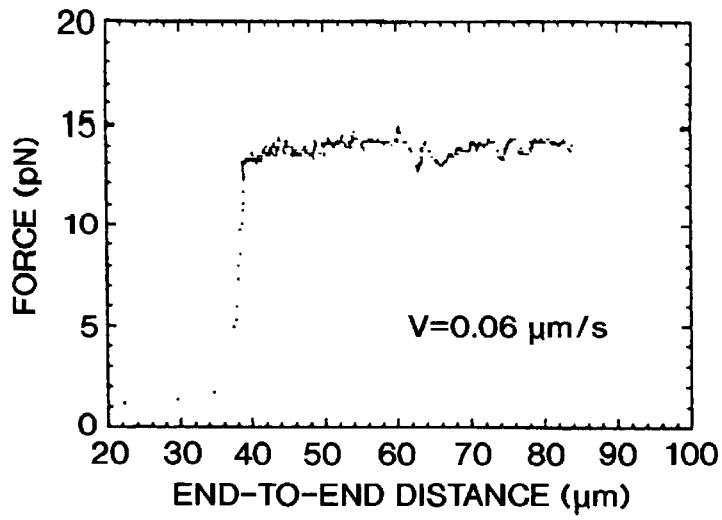
FIG. 6 illustrates the data relating to the force as a function of the end-to-end distance for three measurements (A, B, C) of the same molecule using varying translational speeds. A structure inside the plateau appears more clearly when the translation is slow (FIG. 6A).
Figure 6B:
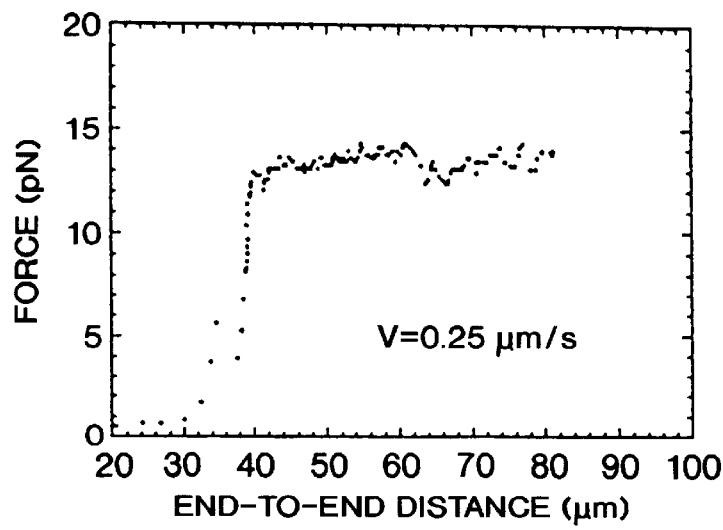
Figure 6C:
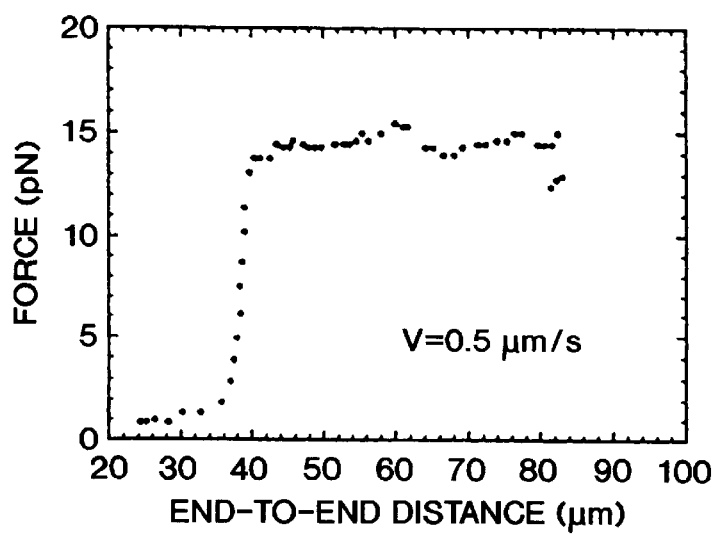

A number of details appear when the speed of movement is slower (FIG. 6). This offers the possibility of optimizing the quality of the force signal by choosing an appropriate sequence of movement as a function of time.

To show that the curve of force as a function of the extension is connected to the base sequence of the λ DNA molecule, a construct was prepared in which the λ DNA intended to be opened, was inverted. This construct called $\Lambda^{-1}$, in contrast to the preceding one which was designated Λ, is prepared so as to open the same type of λ phage molecule, but starting at the other end. By taking the left 5'-3' strand of the λ DNA as reference, the opening of Λ starts from the 5' end and the opening of $\Lambda^{-1}$ starts from the 3' end.

In FIG. 7, the curve of force as a function of the extension of the inverted structure $\Lambda^{-1}$ is compared with that of the direct structure Λ. The components of symmetry appear during the measurement of the force. From this approximate symmetry between Λ and $\Lambda^{-1}$, it is possible to identify details which appear at the origin of the same sequence explored in both directions. The force signal of the inverted construct is placed in the opposite direction in FIG. 7. This makes it possible to compare details of information obtained by the two measurements which appear to be mutually complementary but are not superposed. The arrows indicate the direction opening.

Signature of the Force as a Function of the Sequence

The complete base sequence of the λ molecule is known. In FIG. 8, the mean values of the G-C content along the molecule are represented. Zero on the horizontal axis corresponds to the base pairs which open first in the construct Λ. The measurement of the forces on Λ corresponds to the form characteristic of the local G-C content, as may be seen by comparing FIGS. 7 and 8. A perfect agreement is not expected given that mechanical opening is a complex dynamic process which is not the same for Λ and $\Lambda^{31\ 1}$, and finally that the length of the single strands varies during the opening process and therefore their elasticity varies. From the inspection of the number of characteristics in the opening curve, it is already observed that the resolution of the process is better than 500 bases. The zones rich in GC correspond to higher opening forces compared with the zones low in GC.

Effects of Salt

By carrying out various preliminary measurements with 10 mM Na$^+$, or 1 M Na$^+$ (PB 10 mM Phosphate, 10 mM Na$^+$ or PBS with added salt: 10 mM Phosphate, 1 M Na$^+$), a very weak dependence on the initial level of force $F_0$ necessary to open the DNA is observed. Compared with the standard measurements carried out in PBS (10 nM Phosphate, 150 mM Na$^+$), a tendency for a small increase in $F_0$ (at about 14 pN) in 1 M Na$^+$ and a small decrease in 10 nM Na$^+$ (at about 10 pN), is observed. A higher effect is obviously envisaged at very low salt levels (of the order of one millimolar or submillimolar).

Re-closure of the Strands

Up until now, the force signal appearing when a double helix is opened was essentially studied. When the end-to-end distance decreases, the independent strands become re-paired. As shown in FIG. 9, the force signal acquired during the return step may differ from the signal obtained during the opening. In particular, marked falls occasionally appear in the curve of force as a function of the distance.

A possible interpretation of these effects is that a deferred transient re-pairing exists. Several sources may be envisaged:
1) secondary structures, that is to say a local binding between two strands which are mismatched;
2) particular sequences may induce instabilities;
3) other modifications:
    of other macromolecules (in particular free DNA molecules in solution may become interposed in the closing fork);
    microscopic solids (dust for example).

It is clear that the elasticity of the entire system is involved. In particular, it should be noted that on the instability during closure, the slope of the force/distance curve increases whereas the length of the single strands decreases.

Reproducibility

Measurements were carried out at a high resolution (Analysis II defined above) on the same molecule, at two different times, and at the same mean speed of 160 nm/sec. FIG. 10 presents the result of these two measurements. These results may also be compared with FIG. 8.

Analysis of Signature at High Resolution and at Low Speed

At high resolution (Analysis II defined above) and at low speed, the opening signal exhibits repeats of serrated characteristic units consisting of a slow rise in force, as a function of the movement imposed, followed by an abrupt decrease, a sign of instability.

FIG. 11 is an example of part of a measurement carried out at the mean speed of 40 nm/sec.

The positions and amplitudes of these serrated units depend on the sequence. Thus, as described later, the emergence of an instability may be induced by a highly local variation in the GC content, inducing a point of blockage of opening, followed by a zone of easier opening. After having reached the force threshold necessary to open a hard point, the elastic energy stored in the molecular construct and in the force measuring device will allow the movement of the point of opening along the DNA, even when the position of the moving stage has changed little. Qualitatively, these units become superposed with a base line which depends on the GC proportion in the sequence.

It is thus clear that the signature of the forces results from a complex interaction between the sequences and the mechanical stiffness involved in this measurement. Signatures may be advantageously produced with different stiffnesses.

In the example given, the number of serrations is typically 50, for the opening of a segment of 20 kb. This corresponds to a mean interval between serrations of about 400 bases.

It was observed that the descents of the serrations, observed at a constant movement, correspond to times longer than the characteristic lever response time. On the other hand, and remarkably, the amplitude characteristic of the smaller serrations visible is less than the mean level of vibration of the tip of the lever (subject to external disturbances: acoustic, seismic and the like). The signature is not therefore too sensitive to mechanical disturbances during the measurement.

FIG. 12 presents an additional example of the relationship between the signature of force and the GC content (sliding mean over 500 bases ). The data correspond to a low-speed measurement (20 nm/sec) of the central region of Λ low in GC.

The correspondence between the two curves can be clearly seen but the signature is not identical to a simple averaging.

It can also be seen that the resolution obtained reveals details corresponding to approximately 500 bases.

Modelling of the System and Numerical Resolution

The signature of a given sequence corresponds to a problem of statistical physics, involving thermal agitation, stiffnesses and energies for pairing. The mean observable values (opening force, position of the point of opening, and the like) may be numerically calculated from the system partition function. As will be seen in the text which follows, it is possible, from a known sequence, to numerically calculate the signature. Our model, although simplified, reveals the essential characteristics observed experimentally.

The reference signature(s) of a sequence can therefore be obtained either numerically or experimentally.

An example of a calculation on the opening of the λ phage (corresponding to the preceding Λ configuration) is presented in FIG. 13.

Agreement between simulation and experiment appears on comparing FIGS. 10 and 13.

A magnification of the central zone of the preceding figure is presented at the bottom of FIG. 14. The serrated structure appears clearly. The slow rises correspond to zones where the point of opening moves very little, in contrast with the more rapid descents, where this point of opening moves a lot. This appears in the middle of FIG. 14, where the parameter $<j>$ plotted on the vertical axis is the value which identifies the mean position of the opening zone. The GC content of the corresponding opening zone is plotted on the right.

The calculation of the variance of the position of the opening point, a measurement of the local resolution, is presented at the top of FIG. 14. High variations in resolution which depend on the sequence are observed. This resolution is almost everywhere better than 100 bases. The variance peaks correspond to sites where the signal as force decreases abruptly.

Signature Modifications

Signature and Stiffnesses

The signature depends on the total stiffness of the system, that is to say the total stiffnesses of the system of measurement and the stiffnesses linked to the molecular construct, in particular those of the single strands of the open molecule. A low stiffness promotes large instability events and a high stiffness reduces them. This is theoretically demonstrated in FIG. 15.

Additional Analyses

Mode of Acquisition

A third mode of analysis of the force (called Analysis III) was developed and allows the acquisition of the signal directly (Essevaz-Roulet et al., 1997; Bockelmann et al., 1997). The Analysis III is based on the same principle as the Analysis II defined above, but does not use the intermediate video recordings on a video. The video image in real time of the bead and of the lever is digitized directly on a Macintosh computer provided with a video entry (Mac PPC8600), and a specific software for image analysis extracts therefrom, in real time, the position of the lever. This makes it possible to obtain a file with the deflection of the lever over time, and therefore the force exerted on the molecule during the opening.

Experimental modification of the signature by change in stiffness:

The signature depends on the total stiffness of the system as specified above. When the stiffness increases, the density of information from the signature also increases, that is to say that, for example, the number of peaks is higher. This is demonstrated experimentally by FIGS. 16 and 17 (in both figures, the force in picoNewtons as a function of the end-to-end distance defined above is represented). A portion of the signature obtained with a lever having a stiffness of 2.5 pN/μm on a construct Λ is presented in FIG. 16. FIG. 17 represents the same portion of signature on a construct A, with a lever having a stiffness of about 19 pN/μm.

Comparison of the signature with the sequence of the λ phage DNA.

To compare the signature with the λ phage sequence, the sequence is represented by its G-C base pair density. A sliding Gaussian mean (of given characteristic width L) is measured along the sequence, expressing the mean percentage of G-C bases (from 0 to 100%) along this sequence. To superpose the sequence thus averaged on the signature, it is necessary to give them a common axis. This is done by considering that 1 micrometer of opening (or 1 micrometer of end-to-end distance) corresponds to the opening of about 1000 base pairs. The superposition of two of these curves is represented by FIG. 18. It is the signature (curve plotted as separate points) at 3 micrometers from the beginning of the opening up to 8 micrometers, superposed with the sequence averaged over L=50 bases (curve plotted as a continuous line) between the 3000 and 8000 base index. With this superposition, it is observed in particular that the peaks of the signature are linked to the presence of zones rich in G-C which transiently block the opening. It is possible to deduce therefrom that the signature is sensitive to details of the sequence on scale of about 50 bases.

REFERENCES

1. Bockelmann, U., Essevaz-Roulet, B. & Heslot, F. "Molecular stick-slip motion revealed by opening DNA with piconewton force" (1997) Phys. Rev. Lett. 79, 4489–4492.
2. Bustamante C., Marko J. F., Siggia E. D. and Smith S., "Entropic elasticity of λ-phage DNA", Science 265, p. 1599 (1994).
3. Chu S., Science, 253, 861 (1991).
4. Cluzel P., Lebrun A., Heller C., Lavery R., Viovy J. L., Chatenay D. and Caron F., "A new structural transition in DNA revealed by force measurements on a single molecule", Science 271, pp. 792–794 (1996).
5. Essavaz-Roulet, B., Bockelmann, U. & Heslot, F. "Mechanical separation of the complementary strands of DNA" (1997) Proc. Natl. Acad. Sci. USA 94, 11935–11940.
6. Finer J. T., Simmons R. M., Spudich J. A., Nature 368, 113 (1994).
7. Perkins T. T., Smith D. E., Chu S., "Direct observation of tube-like motion of a single polymer chain", Science, 264, 819–822 (1994).
8. Perkins T. T., Quake S. R., Smith D. E., Chu S., "Relaxation of a single DNA molecule observed by optical microscopy", Science, 264, 822–826 (1994).
9. Perkins T. T., Smith D. E., Larson R. G., Chu S., "Stretching a single tethered polymer in a uniform flow", Science, 268, 83–87 (1995).
10. Rees W. A., Yager T. D., Korte J., von Hippel H., Biochemistry 32, 137 (1993).
11. Smith S. B., Finzi L. and Bustamante C., "Direct mechanical measurement of the elasticity of single DNA molecules by using magnetic beads", Science, 258, 1122 (1992).
12. Smith S. B., Cui Y., Bustamante C., "Overstretching B-DNA", Science, 271, 795–799 (1996).
13. Strick T. R., Allemand J. F., Chiffaudel A., Bensimon D., Bensimon A. and Croquette V., "The elasticity of a single supercoiled molecule", Science 271, (1996).
14. Svoboda K., Schmidt C. F., Schnapp B. J., Block S. M., Nature *365, 721* (1993).
15. Thompson R. E. and Siggia E. D., Europhys. Lett. 31, 335 (1995).
16. Viovy J. L., Heller Ch., Caron F., Cluzel Ph., Chatenay D., C. R. Acad. Sci. Paris 317, 795 (1994).
17. Yin H., Wang M. D., Svoboda K., Landick R., Block S. M., Gelles J., "Transcription against an applied force" Science, 270, pp. 1653–1656 (1996).
18. Zimmerman R. M. and Cox E. C., "DNA stretching on functionalized gold surfaces", Nucl. Acid. Res., 22, 492–497 (1994).

What is claimed is:

1. A method for measuring the force necessary to unpair a nucleic acid duplex, said duplex comprising two nucleic acid sequences having at least one base pair match, comprising:

attaching the 5' end of one of the two sequences to a support 1;

attaching the 3' end of the other sequence to a support 2; and moving apart said supports 1 and 2; and measuring the force necessary to move apart supports 1 and 2;

wherein the point of attachment of the 3' end on the support 2 and the point of attachment of the 5' end on the support 1 are linked together by a molecular string having a length of at least 0.03 μm.

2. Method according to claim 1, wherein the free ends of the nucleic acid sequences are linked to each other.

3. Method according to claim 1, wherein the duplex is locally modified.

4. Method according to claim 3, wherein the local modification is carried out by creating a triplex or a complex or by attachment of a protein.

5. Method according to claim 3, wherein the local modification is carried out by a molecule capable of creating a bridge between the strands of the duplex.

6. Method according to claim 1, wherein at least one strand of the duplex is modified on at least one base after at least one base pair of the duplex is repaired.

7. Method according to claim 1, wherein it is carried out with a buffer which modifies the pairing energies.

8. Method according to claim 1, wherein it is carried out at a temperature which modifies the pairing energies.

9. Method according to claim 1, wherein the supports are chosen from slides, glass or polymer beads or a component of an apparatus for measuring force.

10. Method according to claim 1, wherein at least one of the supports is covered with a matrix which is electronegative over at least part of its surface.

11. Method according to claim 1, wherein one of the supports is moved by a needle or a micropipette or a translational stage or optical tweezers.

12. Method according to claim 1, wherein the DNA duplex to be studied is included in a molecular construct possessing at least two distinct sites for attachment and where the moving apart of these two sites induces the opening of the DNA duplex.

13. Method according to claim 12, wherein the molecular construct comprises a DNA sequence that has been cleaved and subsequently attached to a support.

14. Method according to claim 12, wherein at least one site of the molecular construct adheres to a force sensor directly or via a support and in that this sensor determines the force for opening the duplex when at least one other site of the molecular construct is moved apart and induces this opening.

15. Method according to claim 1, wherein at least one end of the nucleic acid sequence or alternatively one site of a molecular construct is attached to the support through:

a covalent interaction an antigen/antibody interaction, a ligand/receptor interaction, or an avidin or streptavidin/biotin interaction.

16. Method according to claim 14, wherein the force sensor is a lever whose deflection is measured.

17. Method according to claim 14, wherein the variations in force are measured by an atomic force microscope.

18. Method according to claim 14, wherein the force sensor is an optical trap.

19. Method according to claim 18, wherein the optical trap features retroaction.

20. Method according to claim 1, wherein the stiffness of the single strands was modified by addition of other molecules chosen from:

proteins, and oligonucleotides of nucleic acid or of their analogs.

21. Method according to claim 1, the 3' end of the duplex to be characterized is attached to the support 2 via a spacer arm having a length of at least 0.03 μm.

22. Method according to claim 1, wherein the 5' end of the duplex to be characterized is attached to the support 1 via a spacer arm having a length of at least 0.03 μm.

23. Method according to claim 1, wherein the support 1 is selected from the group consisting of a slide, a particle, and a micropipette and the support 2 is a particle.

24. Method according to either of claims 21 or 22, wherein at least one spacer arm is a nucleotide sequence.

25. Method according to claim 24, wherein at least one spacer arm is a double-stranded DNA.

26. Method according to claim 24, wherein at least one spacer arm, by one of its ends, is linked to one of the strands of the double-stranded DNA by a joining oligonucleotide sequence.

27. Method according to claim 21, wherein the DNA duplex to be studied is included in a molecular construct containing at least one spacer arm.

28. Method according to claim 27, wherein the molecular construct with at least one spacer arm comprises a DNA sequence that has been cleaved and subsequently attached to a support.

29. Method according to claim 24, wherein the particles attached to one of the branches of the duplex or of the spacer arm or of the molecular construct are selected by applying a force field or a field gradient thereto.

30. Method according to claim 1, wherein the support 2 is attached to the 3' end of one strand of said duplex, and the support 1 is attached to the 5' end of another strand of said duplex, while the duplex to be characterized has been at least partially denatured and wherein the support 1 was attached beforehand to the 5' end, and the support 2 to the 3' end, and wherein the 3' and 5' ends have been moved apart by a distance of at least 0.03 $\mu$m.

31. Method according to claim 30, wherein the nucleic acid sequences are completely denatured.

32. Method according to claim 30, wherein the sequences are moved apart from each other by the stream of a liquid.

33. Method according to claim 1, wherein the method is applied to the analysis of an unknown DNA or a DNA that has not been fully characterized.

34. Method according to claim 1, wherein the method is applied to the detection of the presence or of the absence of a nucleic acid sequence or of a set of determined DNA sequences in a sample to be tested.

35. Method according to claim 1, wherein the method is applied to the detection of at least one mismatch.

36. Method according to claim 1, wherein the method is applied to the comparison of the force for DNA duplex separation in two DNA samples to be tested.

37. A diagnostic kit for carrying out the method according to claim 1, comprising at least one of the following components:

at least one spacer arm,
  at least one spacer arm molecular construct,
  at least one joining oligonucleotide,
  at least one hairpin-shaped oligonucleotide,
  at least one restriction enzyme,
  at least one molecular construct intended to attach the strands of the duplex to be opened to components of the apparatus for measuring force,
  a support which is attachable to the functionalized end of the spacer arm,
  at least one well,
  at least one slide,
  at least one type of functionalized magnetizable beads intended to be attached to a functionalized component of the duplex to be opened,
  at least one magnet,
  at least one buffer,
  at least one ligation enzyme,
  at least one ligation buffer,
  at least one column for separation by centrifugation, and
  at least one measuring lever.

38. Method of claim 1, wherein the molecular string has a length of between 0.5 and 30 $\mu$m.

39. Method of claim 9, wherein the slides are chosen from glass or polymer coverslips.

40. Method of claim 21, wherein the 3' end of the duplex to be characterized is attached to the support 2 via a spacer arm having a length of between 0.5 and 30 $\mu$m.

41. Method of claim 22, wherein the 5' end of the duplex to be characterized is attached to the support 1 via a spacer arm having a length of between 0.5 and 30 $\mu$m.

42. Method of claim 30, wherein the 3' and 5' ends have been partially moved apart by a distance of between 0.5 and 30 $\mu$m.

43. Method according to claim 27, characterized in that the particles attached to one of the branches of the duplex or of the spacer arm or of the molecular construct are selected by applying a force field or a field gradient thereto.

44. Method according to claim 29, wherein the force field or a field gradient is a magnet or a fluid flow.

45. Method according to claim 43, wherein the force field or a field gradient is a magnet or a fluid flow.

46. Method of claim 1, further comprising bringing together said supports 1 and 2 after the moving apart of said supports 1 and 2.

47. Method of claim 1, wherein at least one of the 5' end or the 3' end of the two sequences is functionalized.

48. Method according to claim 47, wherein the functionalization and/or attachment are carried out in volume delimited by a flat surface for attachment on which is placed a component forming a side enclosure capable of being closed by a cover.

49. Method according to claim 1, wherein the support 2 is selected from the group consisting of a slide, a particle, and a micropipette and support 1 is a particle.

* * * * *

UNITED STATES PATENT AND TRADEMARK OFFICE
CERTIFICATE OF CORRECTION

PATENT NO. : 6,342,353 B1
DATED : January 29, 2002
INVENTOR(S) : Francois Heslot, Baptiste Essevaz-Roulet and Ulrich Bockelmann It is certified that error appears in the above-identified patent and that said Letters Patent is hereby corrected as shown below:

Column 21,
Line 52, "repaired" should read -- uppaired --.

Column 22,
Line 38, "a covalent interaction" should read -- a covalent interaction, --.

Signed and Sealed this

Thirtieth Day of April, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO.    : 6,342,353 B1
DATED         : January 29, 2002
INVENTOR(S)   : Francois Heslot, Baptiste Essevaz-Roulet and Ulrich Bockelmann It is certified that error appears in the above-identified patent and that said Letters Patent is hereby corrected as shown below:

<u>Column 21,</u>
Line 52, "repaired" should read -- unpaired --.

Signed and Sealed this

Eighteenth Day of February, 2003

JAMES E. ROGAN
*Director of the United States Patent and Trademark Office*

SEQUENCE LISTING

```
<160> NUMBER OF SEQ ID NOS:  4

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 1
aggtcgccgc ccaagggact acgagattg                                       29

<210> SEQ ID NO 2
<211> LENGTH: 44
<212> TYPE: DNA
<213> ORGANISM: Artificial Sequence
<220> FEATURE:
<223> OTHER INFORMATION: Description of Artificial Sequence:
      Oligonucleotide
<223> OTHER INFORMATION: 3' biotin

<400> SEQUENCE: 2
aggtcgccgc cccaatctcg tagtcccaaa aaatcagcag taac                      44

<210> SEQ ID NO 3
<211> LENGTH: 12
<212> TYPE: DNA
```

```
<213> ORGANISM: Artificial Sequence
<220> FEATURE:
<223> OTHER INFORMATION: Description of Artificial Sequence:
      Oligonucleotide
<223> OTHER INFORMATION: 3' dig

<400> SEQUENCE: 3
gggcggcgac ct                                                              12

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 4
gggcggcgac ctagcgaaag ct                                                   22
```